US010850097B2

United States Patent
Hadlock et al.

(10) Patent No.: US 10,850,097 B2
(45) Date of Patent: Dec. 1, 2020

(54) ELECTRICAL NEURAL BLOCKADE AND FUNCTIONAL STIMULATION OF DYSFUNCTIONAL OR TRANSFERRED NERVES

(71) Applicant: Massachusetts Eye and Ear Infirmary, Boston, MA (US)

(72) Inventors: Theresa A. Hadlock, Concord, MA (US); Nathan T. P. Jowett, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 179 days.

(21) Appl. No.: 16/069,341

(22) PCT Filed: Jan. 13, 2017

(86) PCT No.: PCT/US2017/013537
§ 371 (c)(1),
(2) Date: Jul. 11, 2018

(87) PCT Pub. No.: WO2017/124019
PCT Pub. Date: Jul. 20, 2017

(65) Prior Publication Data
US 2019/0022383 A1    Jan. 24, 2019

Related U.S. Application Data

(60) Provisional application No. 62/279,487, filed on Jan. 15, 2016.

(51) Int. Cl.
*A61N 1/36* (2006.01)
*A61N 1/06* (2006.01)

(52) U.S. Cl.
CPC .......... *A61N 1/36003* (2013.01); *A61N 1/06* (2013.01); *A61N 1/3614* (2017.08); *A61N 1/36053* (2013.01); *A61N 1/36139* (2013.01)

(58) Field of Classification Search
None
See application file for complete search history.

(56) References Cited

U.S. PATENT DOCUMENTS 8,024,044 B2   9/2011   Kirby et al.
8,060,208 B2   11/2011  Kilgore et al.
(Continued)

FOREIGN PATENT DOCUMENTS

WO   2017/124019 A1   7/2017

*Primary Examiner* — Brian T Gedeon
(74) *Attorney, Agent, or Firm* — Mintz Levin Cohn Ferris Glovsky and Popeo, P.C.

(57) ABSTRACT

Methods and devices are provided for electrical neural blockade and stimulation of dysfunctional or transferred nerves. For example, a method is provided including identifying a dysfunctional or transferred nerve, attaching an electrode array to the dysfunctional or transferred nerve proximal to the target musculature, delivering an electrical neural blockade signal, and stimulating the dysfunctional or transferred nerve distal to the point of neural blockade. A system is also provided with an electrode array configured to attach proximally to a dysfunctional or transferred nerve and deliver an electrical neural blockade signal with a neuromuscular stimulating electrode array placed distal to the point of neural blockade, and a processor in communication with the electrode arrays and configured to provide stimulation instructions based on the detected activity of the other neuromusculature. A method is further provided for identifying and treating dysfunction arising from aberrant neural regeneration for which contralateral paired neuromusculature exists.

20 Claims, 14 Drawing Sheets

(56) References Cited

U.S. PATENT DOCUMENTS

| | | |
|---|---|---|
| 8,843,188 B2 | 9/2014 | Kilgore et al. |
| 8,983,614 B2 | 3/2015 | Kilgore et al. |
| 9,008,800 B2 | 4/2015 | Ackermann, Jr. et al. |
| 9,119,966 B2 | 9/2015 | Franke et al. |
| 9,370,654 B2 * | 6/2016 | Scheiner .............. A61N 1/0556 |
| 2005/0149154 A1 | 7/2005 | Cohen et al. |
| 2009/0202387 A1 | 8/2009 | Dlugos, Jr. et al. |
| 2011/0125216 A1 | 5/2011 | Kilgore et al. |
| 2011/0152956 A1 | 6/2011 | Hincapie Ordonez et al. |
| 2014/0336728 A1 | 11/2014 | Franke et al. |
| 2015/0174397 A1 | 6/2015 | Bhadra et al. |

* cited by examiner

ELECTRICAL NEURAL BLOCKADE AND FUNCTIONAL STIMULATION OF DYSFUNCTIONAL OR TRANSFERRED NERVES

RELATED APPLICATIONS

This application is a national stage application filed under 35 U.S.C. § 371, of International Patent Application No. PCT/US2017/013537, filed Jan. 13, 2017, which claims the benefit of and priority under 35 U.S.C. § 119(e) to U.S. Provisional Application No. 62/279,487, filed Jan. 15, 2016, which is incorporated herein by reference in its entirety.

FEDERALLY SPONSORED RESEARCH AND DEVELOPMENT

This invention was made with government support under NIH 5R01NS071067-04 awarded by the National Institutes of Health. The government has certain rights in the invention.

FIELD

Methods and devices are provided for electrical neural blockade and stimulation of dysfunctional or transferred nerves, for example for use in humans.

BACKGROUND

Recovery from high grade peripheral motor nerve injury (e.g., Sunderland class III or higher) is associated with varying degrees of loss of normal control over the activation of target muscles. Such loss of control is the result of aberrant re-innervation of motor axons to target muscles, aberrant sprouting of axon terminals to multiple target muscles, and/or other factors that are not completely understood. The result of such aberrant neural recovery in the recurrent laryngeal nerve is the loss of coordinated movement of vocal fold adductor and abductor muscles, producing functional impairment in vocalization, breathing, and swallowing. In the brachial plexus, the result of such aberrant neural recovery is varying degrees of loss of fine and gross motor skills of the hand and arm. The result of such aberrant neural recovery in the face is asymmetric and involuntary facial movements with voluntary and spontaneous emotive responses, sometimes referred to as synkinesis, as well as facial muscular contracture. For example, when a patient voluntarily smiles, the patient may experience an involuntary contraction of the eye muscles causing the eye to squint. Further, a patient may involuntarily close an eye, pucker their mouth, experience massive neck contraction with smiling, or have mid-facial and neck contraction when closing eyes. These issues can arise, for instance, after spontaneous or surgery-assisted recovery from acute facial palsy arising from traumatic, vascular, infectious, neoplastic, and/or iatrogenic insults to the facial nerve.

Surgical reanimation following high grade peripheral motor nerve injury, or congenital absence of a nerve and hence its target muscles, may also entail nerve or nerve and functional muscle transfer procedures. Such nerve transfer procedures are inherently subject to undesirable activation of the target muscle due to normal physiologic action of the transferred nerve. For example, in patients who undergo transfer of free muscle to the face to restore a facial expression such as a smile, neural innervation of the transferred muscle is often provided by nerve transfer of a regional nerve, such as the masseteric branch or segment of the trigeminal nerve. Activation of the transferred muscle may then be volitionally achieved through a conscious bite effort when a smile is desired. However, the muscle will also activate during normal prandial activity, resulting in highly disfiguring facial twitching while eating.

These issues are not limited to the facial region. A patient may experience involuntary and abnormal muscular activation resulting in contractures, loss of normal motor coordination, and/or undesirable muscle activation throughout the body as a result of various injuries, disorders, or surgical nerve transfer procedures to nerves throughout the body. Current management options for such sequelae include physiotherapy, botulinum toxin injection, and highly selective distal branch or segment neurectomy. Although helpful, such procedures do not restore normal physiologic function. For example, in the facial region, facial disfigurement with movement will remain obvious. Thus a sufferer remains unable to fully control his or her facial disfigurement and facial expressions, resulting in functional, communication, and psychosocial impairment, with profound negative impact on quality of life and emotional well-being. Similarly, loss of normal control over muscle activation in any other region of the body can often result in profound functional and psychosocial impairment.

SUMMARY

Accordingly, there remains a need for methods and devices for electrical blockade of undesirable neural activation together with functional electrical stimulation of dysfunctional or transferred nerves, especially for use in humans. Various methods, systems, and devices are provided for electrical neural blockade and functional stimulation of dysfunctional or transferred nerves.

In one aspect, a method of treating undesired neural activity in a subject is provided including identifying dysfunctional or transferred nerve, nerve segment(s), and/or neuromusculature. The method also includes attaching an electrode array to the dysfunctional or transferred nerve, nerve segment(s), and/or neuromusculature, for example through the use of an electrode array, to deliver electrical signals, such as high frequency alternating current, to block undesirable neural activity. The method can include delivering a localized electrical neural blockade signal through the electrode array to inhibit propagation of neural depolarization at that point. The method also can include delivering a variable stimulus signal to the dysfunctional or transferred neuromusculature in a functional manner distal to the point of neural blockade, and/or delivering an electrical signal through the same electrode array or separate electrode array or arrays to proportionally stimulate the target musculature or nerve or nerve segment distal to the point of neural blockade (i.e. closer to the target musculature) in order to evoke the desired degree of muscle activation.

The method can vary in numerous ways. For example in some embodiments the electrical neural blockade signal comprises high frequency alternating current or a signal able to achieve localized and reversible neural blockade. In some embodiments, the method includes attaching a detector to other neuromusculature whose activity is be used to drive the timing and degree of stimulation of the dysfunctional or transferred neuromusculature. The method can also include attaching a detector to, on, around, adjacent to, or within other neuromusculature in order to detect a signal indicating the activity of said neuromusculature. In the face in a subject with unilateral facial palsy, this could entail placement of a detector to record the activity of the contralateral (i.e. healthy-side) paired neuromusculature. In the larynx in a subject with unilateral vocal fold palsy, this could entail placement of a detector to detect the contralateral (i.e. healthy-side) paired neuromusculature activity, placement of a detector near the pleural space to detect pressure or force changes indicating the activity of the diaphragm and subsequently the phase of respiration, and/or placement of a detector on adjacent neuromusculature within the neck to indicate the activity of muscles associated with swallowing. In some embodiments, stimulating the dysfunctional or transferred neuromusculature can include stimulating the dysfunctional or transferred neuromusculature based on detected activity of other neuromusculature. Stimulation of the dysfunctional or transferred neuromusculature can also include stimulating the dysfunctional or transferred neuromusculature based on the detected signal indicating the activity of another neuromusculature. In the face, the dysfunctional or transferred neuromusculature can be a facial nerve and the target facial muscles and the healthy neuromusculature can be a contralateral facial nerve branch or segment or contralateral facial muscle. In the larynx, the dysfunctional or transferred neuromusculature can be the recurrent laryngeal nerve and the target vocal fold muscles, and the healthy nerve-muscle complex can be a contralateral recurrent laryngeal nerve branch or segment or contralateral laryngeal muscle.

In various embodiments, the dysfunctional or transferred neuromusculature can include a facial nerve or facial nerve segment(s) or respective or corresponding target musculature and the other neuromusculature can include a paired contralateral facial nerve or facial nerve segment(s) or respective or corresponding target musculature. In other embodiments, the dysfunctional or transferred neuromusculature can include a vagal nerve or vagal nerve segment(s) or respective or corresponding vagal nerve target musculature and the other neuromusculature can include a paired contralateral vagal nerve or phrenic nerve or a segment or segments of the vagal nerve or phrenic nerve or respective or corresponding vagal or phrenic nerve target musculature. In various embodiments, the dysfunctional or transferred neuromusculature can include a transferred nerve to native musculature or transferred musculature, and the other neuromusculature can include an other neuromusculature Detecting the activity of other neuromusculature can also include detecting the emitted electrical signals of the neuromusculature. Detecting activity of the other neuromusculature can include detecting signals respective or corresponding to displacement, impedance, force, or pressure changes that arise due to the activity of the other neuromusculature. In some other embodiments, detecting the activity of other neuromusculature can include detecting signals that correspond to changes in tissue position resulting from activity of the neuromusculature. In some other embodiments, detecting the activity of other neuromusculature can include detecting signals that correspond to changes in pressure or force. Delivery of the electrical neural blockade signal and delivery of a variable stimulation signal to the dysfunctional or transferred neuromusculature to achieve proportional control of muscle activation can be performed during waking hours and/or sleeping hours of the subject. Delivery of the electrical neural blockade signal and delivery of a stimulating signal to the dysfunctional or transferred neuromusculature to achieve functional or desirable activation can also be performed only during waking hours of the subject in some embodiments or only during sleeping hours in some other embodiments or both during waking and sleeping hours in other embodiments.

In another aspect, a system of treatment for a dysfunctional or transferred nerve-muscle complex is provided with electrode arrays, a processor, and a signal generator. A neural electrode array is configured to attach to a dysfunctional or transferred nerve in order to deliver an electrical neural blockade signal from the signal generator. One or more separate electrode arrays are placed distally onto branches or segments of the dysfunctional or transferred nerve or the target musculature in order to deliver variable electrical stimulation signals from the signal generator in order to activate the target musculature to the desired degree. The electrical neural blockade signal may be delivered continuously or for shorter periods of time, such as seconds, minutes, or hours at a time in communication with and according to the configuration of the processor, while the variable electrical stimulation signals to distal nerve branches or segments or target muscles may be delivered in communication with and according to the configuration of the processor. A system of neuromusculature treatment or device for treatment can also be provided having an electrode array configured to attach proximally along a dysfunctional or transferred nerve(s), nerve segment(s), and/or neuromusculature and deliver an electrical neural blockade signal. The system has a stimulating nerve or muscle electrode array configured to attach distally along the dysfunctional or transferred neuromusculature and apply a variable stimulatory signal to the dysfunctional or transferred neuromusculature. The system also has a processor in communication with a signal generator, a power supply, the proximal electrode array, and the distal stimulating nerve or muscle electrode array and configured to provide stimulation instructions to the distal stimulating nerve or muscle electrode array and neural blockade instructions to the proximal electrode array.

The system or device for treatment can have various embodiments. For instance, the system can further include a detector configured to detect the activity of contralateral neuromusculature respective or corresponding to the dysfunctional or transferred neuromusculature and configured to detect signals respective or corresponding to the activity of other neuromusculature. The processor in such an embodiment is in communication with the detector and is configured to provide instructions to the signal generator to deliver variable stimulatory signals to the dysfunctional or transferred neuromusculature based on the input signal arising from the detector of the activity of the other neuromusculature. In one embodiment, a detector is provided that is configured to detect activity of other neuromusculature where the processor is in communication with the detector and is configured to provide functional stimulation instructions to the distal nerve or muscle stimulating electrode array based on activity signals detected by the detector. In some embodiments, the activity of a single other neuromuscular complex will be detected, while in other embodiments, the activity of multiple other neuromuscular complexes will be detected through the use of multiple detectors. In a similar fashion, variable stimulation signals will be delivered to a single dysfunctional or transferred neuromuscular complex to achieve the desired amount of activation in one embodiment, and to multiple dysfunctional or transferred neuromuscular complexes to achieve the desired amounts of activation in other embodiments. The dysfunctional or transferred neuromusculature can be the main trunk of the facial nerve, repaired facial nerve, or a cranial nerve transferred to the distal portion of the facial nerve and its target muscles, or distal branches or segments of the facial nerve and their target musculature. In various embodiments, the dysfunctional or transferred neuromusculature includes a neuromuscular unit that corresponds to a paired contralateral neuromuscular unit. The detector can also be configured to detect emitted electrical activity of other neuromusculature such as healthy side facial musculature. In other embodiments, the detector can be configured to detect displacement changes of other neuromusculature. In other embodiments, the detector can be configured to detect pressure or force changes respective or corresponding to the activity of other neuromusculature. The system can include detecting activity of the other neuromusculature includes detecting signals respective or corresponding to displacement, impedance, force, or pressure changes that arise due to the activity of the other neuromusculature. The system can also be enabled during waking and/or sleeping hours of a subject. Alternatively in some embodiments, the system can only be enabled during waking hours of a subject or only during sleeping hours in some other embodiments. In some embodiments, the system can be selectably enabled during waking hours and/or sleeping hours with the selection being made before implantation and/or in real-time during use. In various embodiments, the dysfunctional or transferred neuromusculature can include a facial nerve or facial nerve segment and its target musculature and the other neuromusculature comprises a contralateral facial nerve or facial nerve segment and its target musculature.

In some embodiments, the dysfunctional or transferred neuromusculature includes a vagal nerve or vagal nerve segment(s) or respective or corresponding vagal nerve target musculature and the other neuromusculature includes a paired contralateral vagal nerve or phrenic nerve or a segment or segments of the vagal nerve or phrenic nerve or respective or corresponding vagal or phrenic nerve target musculature.

In another aspect, a method of identifying a dysfunctional nerve or nerve branch(es) or segment(s) in a subject with abnormal muscle activity is provided. The dysfunctional or transferred nerve can be a variety of different nerves, such as the main trunk of the facial nerve, branches, or segments thereof, or the vagal nerve, branches, or segments thereof, such as the recurrent laryngeal nerve, or the brachial plexus or branches or segments thereof, or other regions throughout the body. The dysfunctional muscle can be a variety of muscles, such as the orbicularis oculi muscle, the vocal fold adductor or abductor muscles, or wrist pronator muscles. The method includes identifying nerve branches or segments to the muscle demonstrating abnormal activity and placing electrode arrays on or around them. The method further includes eliciting the abnormal muscle activity. The method further includes attempts at eliciting the abnormal muscle activity while an electrical neural blockade signal is delivered through the electrode array or arrays. In some embodiments, the method includes attempts at eliciting the abnormal muscle activity while electrical neural blockade signals are delivered to some of the nerve branches or segments but not to others.

In another aspect, a method of treating nerve dysfunction in a subject with abnormal muscle activity is provided including identifying a dysfunctional or transferred nerve or nerve branches or segment along which undesirable neural signals pass. The dysfunctional or transferred nerve could be the main trunk of the facial nerve or branches or segments thereof, or the vagal nerve or branches or segments thereof, such as the recurrent laryngeal nerve. The method also includes attaching an electrode array on the dysfunctional or transferred nerve or nerve branches or segments. The method further includes the delivery of an electrical neural blockade signal, such as high frequency alternating current, through the electrode array in order to block undesirable neural signals. The method also includes identifying respective or corresponding distal nerve branches or segments or target muscles of the contralateral healthy-side nerve, and the subsequent placement of a detector or detectors on said distal nerve branch(es) or segment(es) or target muscle(s) in order to measure a signal that corresponds to activation of said target musculature. Additionally, the method includes delivery of an electrical stimulation signal to distal branch(es) or segment(s) of the dysfunctional or transferred nerve or their target muscle fibers that varies according to the detected activity of the contralateral healthy nerve branch(es) or segment(s) or target muscle(s) in order to achieve the desired amount of muscle activation.

A method of treating nerve dysfunction in a subject with unilateral aberrant neuronal regeneration or nerve transfer leading to loss of normal muscle control or function for which contralateral paired neuromusculature exists is provided that includes identifying a dysfunctional or transferred nerve or segment(s) along which undesirable neural signals pass. The method also includes identifying the contralateral paired neuromusculature. The method further includes attaching an electrode array on the dysfunctional or transferred nerve or segment(s) proximal to its target musculature, and delivering an electrical neural blockade signal from the neural electrode array to block propagation of neural signals. The method also includes detecting activity of the contralateral paired neuromusculature, and stimulating the dysfunctional or transferred nerve or segment(s) or target muscle distal to a point of neural blockade to mirror the activity of the contralateral paired musculature.

The method can vary in a variety of ways. For example, the dysfunctional or transferred nerve or segment(s) can include a facial nerve or facial nerve segment(s) or transferred cranial nerve to drive facial expression and respective or corresponding target musculature and the contralateral paired neuromusculature can include a paired contralateral facial nerve or facial nerve segment(s) or respective or corresponding target musculature. The dysfunctional or transferred nerve or segment(s) can also include a vagal nerve or segment(s) or respective or corresponding target musculature and the contralateral paired neuromusculature compromises a paired contralateral vagal nerve or segment(s) or respective or corresponding target musculature. As another example, detection of the activity of a paired-contralateral healthy neuromusculature can include detecting the emitted electrical activity of that neuromusculature. Detecting activity of the contralateral paired neuromusculature can include detecting emitted electrical activity of a contralateral paired nerve segment or target muscle. Detecting activity can include detecting electromyography activity through implanted electrodes. Detecting activity of the contralateral paired neuromusculature can include detecting signals respective or corresponding to displacement, impedance, force, or pressure changes that arise due to the activity of the contralateral paired neuromusculature. Detecting activity of the contralateral paired neuromusculature can include detecting displacement changes by measuring impedance changes of the contralateral healthy facial muscle or placing a contact probe overlying a contralateral healthy facial muscle. Delivering the electrical neural blockade signal and stimulating the dysfunctional or transferred nerve or segment(s) can also be performed during waking hours of the subject, during sleeping hours of the subject, or both.

Detecting emitted electrical activity can also include detecting electromyography activity or nerve action potentials of the paired contralateral neuromusculature through implanted electrode arrays. In other embodiments, detecting the activity of paired-contralateral neuromusculature can include detecting of signals that change according to tissue displacement resulting from activity of the neuromusculature. Detection of displacement changes can also include measurement of impedance changes of the contralateral paired musculature or by placement of a contact probe or probes overlying the paired musculature. Delivery of an electrical signal to the dysfunctional or transferred nerve in order to block transmission of neural activity together with delivery of functional stimulatory signals to distal nerve branches or segments or target muscles can also be performed during waking and/or sleeping hours of the subject. In other embodiments, delivery of an electrical signal to the dysfunctional or transferred nerve in order to block transmission of neural activity together with delivery of functional stimulatory signals to distal nerve branches or segments or target muscles can only be performed during waking hours of the subject or only during sleeping hours in some other embodiments. The electrical signal to achieve neural blockade can be high frequency alternating current.

In another aspect, a device for neuromusculature treatment is provided that has a blockade electrode array, a stimulating electrode array, a signal generator, a power supply, and a processor. The blockade electrode array is configured to deliver an electrical neural blockade signal, and the stimulating electrode array is configured to apply a variable stimulatory signal. The processor is in communication with the signal generator, the power supply, the blockade electrode array, and the stimulating electrode array and is configured to provide stimulation instructions to the stimulating electrode array and neural blockade instructions to the blockade electrode array.

The device can have numerous variations. For example, the device can also have a detector configured to detect neural activity. In such an example, the processor can be in communication with the detector and can be configured to provide functional stimulation instructions to the stimulating electrode array based on signals detected by the detector. In other examples, the detector can be configured to detect signals corresponding to displacement, impedance, force, or pressure changes.

The methods, systems, and devices described herein are useful for human therapy as well as veterinary therapy for other mammalian subjects such as companion animals, e.g., dogs, cats, or performance or working animals such as horses.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
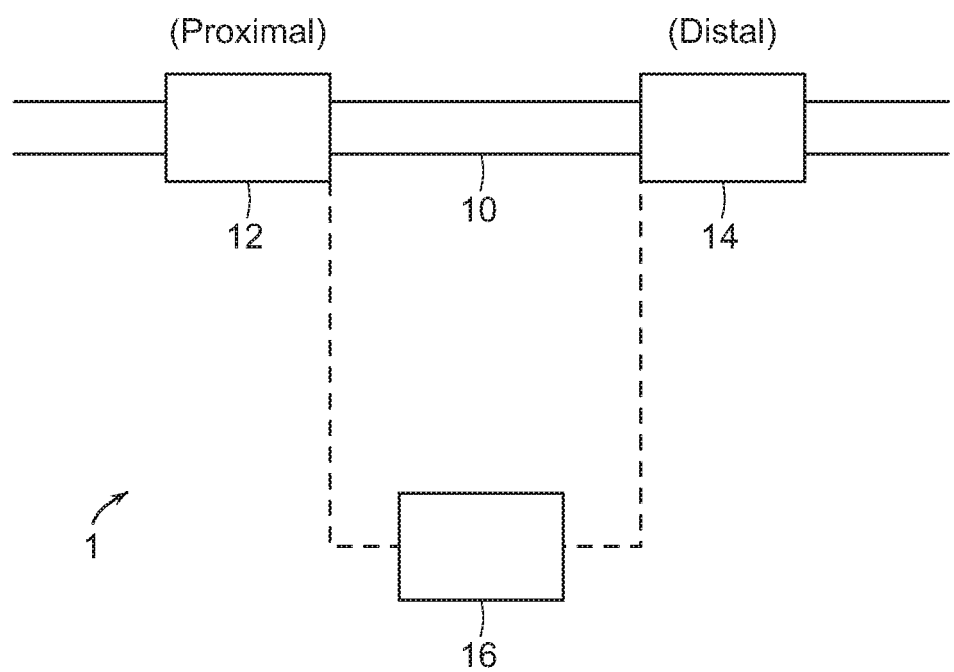
FIG. 1 illustrates an exemplary embodiment of a system and/or device to treat dysfunctional or transferred neuromusculature.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for electrical neural blockade and stimulation of dysfunctional or transferred nerves. Generally artificial reanimation of a nerve injury is provided. This artificial approach may be combined with current surgical approaches, such as cable grafting of nerve defects, direct end-to-end coaptation of dysfunctional or transferred nerves, or nerve transfer procedures to optimize outcomes.

Synkinesis, development of linked or unwanted facial movements, may occur in people who are recovering from facial palsy. For example, it may occur after trauma and may be manifested through involuntary muscular movements accompanying voluntary movements. For example, voluntary smiling will induce an involuntary contraction of the eye muscles causing the eye to squint when the subject smiles. For example, electrical inhibition of synkinesis in the face is provided and coupled with distal functional electrical stimulation of the distal nerve branch or segment or target muscle. While reanimation of dysfunctional nerves has been attempted before, the approach provided herein allows for selective, localized, and rapidly reversible electrical neural blockade, for example by utilizing high frequency alternating current (HFAC) delivered through implanted nerve cuff electrode arrays. This allows for a non-ablative means of neural blockade of dysfunctional or transferred nerves, while maintaining axonal input to the affected muscles. Such selective neural blockade allows for the prevention of propagation of undesirable or aberrant neural signals from dysfunctional or transferred nerves, without affecting distal nerve or target muscle excitability. This provides a means of blocking signals from dysfunctional or transferred nerves, such as synkinetic signals in the face for example, or normal physiologic signals from transferred nerves, such as those that arise while chewing through a transferred masseteric branch or segment of the trigeminal nerve or through manipulation of the food bolus through a transferred hypoglossal nerve for example, while maintaining the ability to achieve muscle contraction when desired through an electrode placed distally on the nerve, nerve branch or segment, or target muscle. Such an inhibitory signal can be left on for long periods of time, with intermittent stimulatory signals delivered as needed (for example to match movements of a healthy contralateral facial nerve when stimulation of a dysfunctional or transferred facial nerve is desired). This approach eliminates the problem of an 'onset response' and an 'offset response' when electrical neural blockade is switch on or off, respectively.

Generally high frequency alternating current (HFAC) will be distinct from "high frequency blockade" as a means to induce localized neural blockade. Alternating current is an electric current in which the flow of electric charge periodically reverses direction, while generally low frequency is under about 0.1 Hz, medium frequency is about 0.1 Hz to about 500 Hz, and high frequency is over 500 Hz and typically less than 100 kHz for such purposes. The waveform is typically sinusoidal. The peak-to-peak amplitude may be delivered in voltage-controlled or current controlled fashion. Typical peak-to-peak amplitudes when the voltage is controlled range from 1 V to 10 V, while typical peak-to-peak amplitudes when the current is controlled range from 0.1 to 2 mA. However, these ranges are only provided as examples and are not intended to limit the present invention. These ranges can be adapted based on the scenario, situation, and/or patient being treated. An electrode array (such as a bipolar or multipolar nerve cuff electrode) or similar device that is in intimate contact with a nerve is beneficial to deliver HFAC as the electrical neural blockade should be localized to a very specific branch or segment of a nerve branch or segment in order to be effective and in order to maintain distal excitability (or control) of the nerve. The HFAC neural blockade signal can also be confined between electrodes spaced very closely together (such as two neighboring electrodes in a nerve cuff electrode array such as a bipolar or multipolar nerve cuff) and that envelop, or nearly envelop, the nerve in order to generate adequate field strength of the electromagnetic field necessary for electrical neural blockade. Additionally, the HFAC neural blockade should be proximal to the stimulation signals to work in practice. Induction and cessation of HFAC neural blockade can demonstrate a transient muscle response, whereby a muscle twitch or brief tetanic contraction is seen on induction, and on cessation, with a concurrent transient neural blockade remaining in place on the order of tens to hundreds of milliseconds after cessation of the HFAC current. As such, use of rapid 'on/off' neural blockade in real-time to block conduction past a branch or segment point from a proximal stimulation pulse is not ideal at the least, and completely unfeasible at worst. The electrical neural blockade should thus be proximal and can be "always on" (while the patient is, for example, awake, socializing, and wanting to make use of the desired implant, etc.) in order to avoid such onset/offset responses. As an illustrative example, a sine wave with a peak-to-peak voltage amplitude of approximately 3 to 10 V using constant voltage stimulation at frequencies above 5 kHz (for example, 30 kHz) produces effective neural blockade. See for example U.S. Pat. No. 8,060,208 entitled "Action potential conduction prevention," U.S. Pat. No. 8,843,188 entitled "Adjustable nerve electrode," U.S. Pat. No. 8,983,614 entitled "Onset-mitigating high-frequency nerve block," U.S. Pat. No. 9,008,800 entitled "Separated-interface nerve electrode," and U.S. Pat. No. 9,119,966 entitled "Systems and methods that provide an electrical waveform for neural stimulation or nerve block," all of which are incorporated herein by reference in their entirety.

For practical and power saving reasons, a single proximal electrode array in the form of a nerve cuff electrode (NCE) can be applied around the main trunk of the dysfunctional or transferred nerve or nerve to be controlled (e.g., a transferred nerve) while using multiple stimulatory NCEs or direct muscle stimulation electrodes distal to the point of blockade. In this fashion, all physiologic neural impulses will be blocked, allowing for complete control of the nerve and target muscles through functional electrical stimulation (FES) paradigms. Such an approach is also advantageous in that the retrograde propagation of any potential afferent signals from indwelling sensory nerves that might be triggered by distal functional electrical stimulation (with resultant discomfort) will be blocked.

As an illustrative example, movement of healthy, intact musculature that corresponds to any dysfunctional or transferred musculature can be detected by a variety of means, including EMG electrodes placed directly into on onto the surface of the muscle, or neural cuffs placed along distal branches or segments of nerve branches or segments associated with the healthy musculature. The resultant signals regarding the contraction of this healthy musculature, which carries information on the strength of contraction or lack thereof of each of the individual muscles—would then be passed on to a multichannel signal processor, and over to the dysfunctional or transferred nerve through a receiver (via a wired or wireless antenna connection), then out to a multichannel signal generator sending either inhibitory (to the proximal portion of the terminal nerve to a given target muscle) or stimulatory (to the distal portion of the terminal nerve to the target muscle or directly the target muscle itself). Total signaling processing time would fall under about 40 ms, such that the human eye could not observe a difference in contraction between the dysfunctional or transferred and functional musculature, creating the illusion of evoked muscular contraction on a simultaneous time-scale with that of the sensed muscle. This approach could be applied to a variety of musculature, such as facial musculature by monitoring the behavior of contralateral facial muscles and mimicking the musculature behavior of healthy muscles and/or nerves to dysfunctional or transferred ones. In this way, reanimation of symmetric expression would be achieved. Higher-order signal processing paradigms could also be utilized to detect the onset of a desired asymmetric movement through analysis of the detected activity of multiple sensed nerve-muscle units; for example, in the face expression of suspicion on the healthy-side could be detected through concurrent analysis of brow, eyelid, and midface displacement. Asymmetric neural stimulus signals could then be outputted to the diseased-side in order to achieve the desired asymmetric expression.

Another illustrative example of the combination of neural blockade with functional electrical stimulation is in the setting of otherwise healthy neuromuscular interfaces, where normal discharge of a nerve can result in undesirable consequences. An example of such a situation is in obstructive sleep apnea, where the normal firing of the hypoglossal nerve during sleep (which carries fibers that, among other actions, cause retraction or protraction of the tongue) may result in obstruction of the airway at the oropharyngeal level. Many approaches to FES of the hypoglossal nerve during sleep for the management of sleep apnea involve placement of an implantable neural cuff around distal branches or segments of the hypoglossal nerve, which are primarily selective for tongue protractor muscles, in order to deliver stimulatory signals alone (as further described in U.S. Pat. No. 8,024,044 filed Jun. 28, 2007 and entitled "Method and apparatus for hypoglossal nerve stimulation," incorporated herein by reference in its entirety). However, such an approach does not prevent simultaneous physiologic or undesirable FES co-activation of neural fibers that result in contraction of opposing tongue retractor muscles. The addition of a neural blockade signal delivered either in proximal fashion to the main trunk of the hypoglossal nerve or in parallel fashion to distal branches or segments that primarily control tongue retractors can provide a means to enhance the efficacy of the FES signal delivered to the distal neural branches or segments that control tongue protraction.

Figure 2:
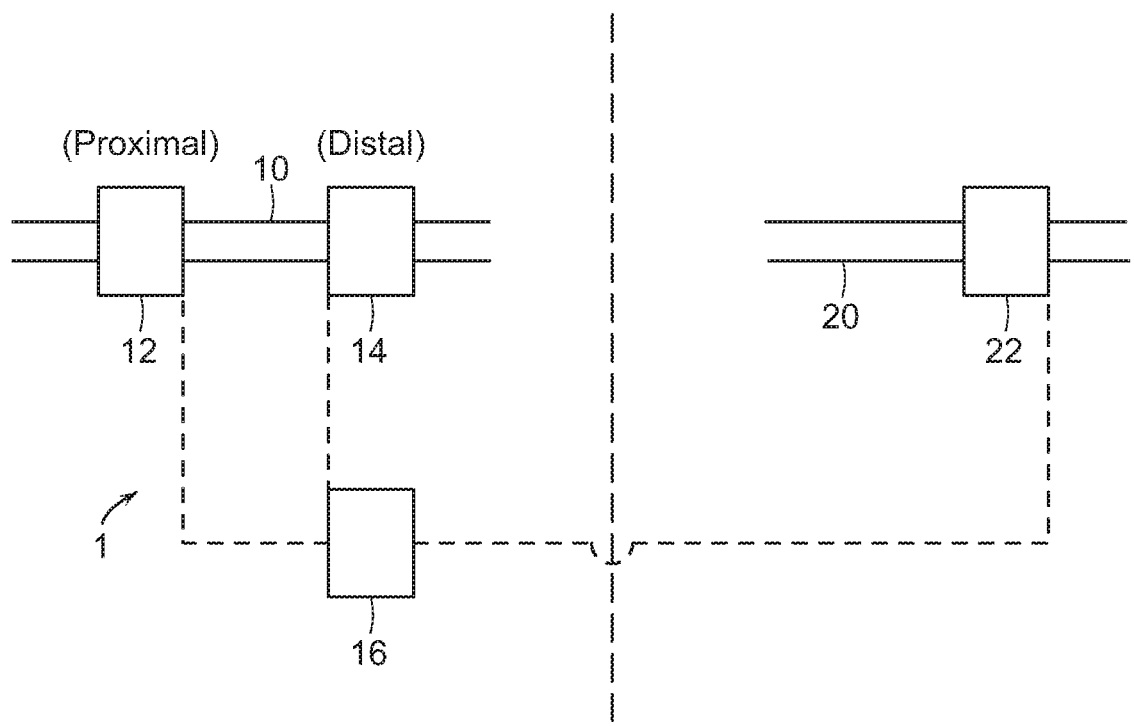
FIG. 2 illustrates the system or device of FIG. 1 with a detector.

FIG. 1 illustrates an embodiment of a system 1 of neuromusculature treatment that can be used in humans with a proximal neural electrode array 12, a distal nerve or muscle electrode array or arrays 14, and a processor coupled to a signal generator and power source 16. The proximal neural electrode array 12 attaches proximally to a dysfunctional or transferred nerve 10 and delivers an electrical neural blockade signal such as high frequency alternating current from a signal generator to which the distal leads are attached. The distal nerve or muscle electrode array 14 attaches distally to the dysfunctional or transferred neuromusculature 10 and delivers a stimulatory signal to the neuromusculature 10. The processor 16 communicates with the both the proximal 12 and distal electrode arrays 14 and provides blockade and stimulation instructions to the electrode arrays 12 and 14. As illustrated in FIG. 2, a detector 22 detect the activity of other neuromusculature 20 that may represent contralateral paired neuromusculature corresponding to 10 or other neuromusculature. The detector 22 detects activity signals of the other neuromusculature(s) 20 and communicates with the processor 16. The processor 16 then provides stimulation instructions to the distal nerve or muscle electrode arrays 14 based on the activity signals detected by the detector 22.

The neuromusculature can vary depending on the embodiment. For example, the dysfunctional or transferred neuromusculature can be a distal branch or segment of the facial nerve and its target muscle, and the other neuromusculature can be a contralateral distal facial nerve branch or segment or target muscle. However, the neuromusculature can be various nerves and/or muscles throughout the body capable of experiencing electrical neural blockade and stimulation. The detector detects activity signals in a variety of ways. For instance, the detector can detect emitted electrical activity of the other neuromusculature. The detector could also detect displacement changes of the other neuromusculature. The detector could also detect force or pressure changes associated with the activity of the other neuromusculature.

The system can be enabled at all times, during waking hours, and/or only during waking hours. A patient may desire to experience stimulation and blockade only during waking hours or only while in public depending on the reasoning behind the patient's use of the system. For example, if the patient is using the system due to embarrassment over experiencing synkinetic signals around other people, the patient may only desire to use the system in public or only during waking hours. The system can take a variety of different forms. In some embodiments, the proximal neural electrode array or arrays, the distal nerve or muscle electrode array or arrays, the processor, the signal generator, the power source, and the detector can all be in communication with each other. In various embodiments, signal acquisition, processing, and output can be performed using an external or implantable multichannel receiver/stimulator/processor using battery or inductive-coupling to power the device. In further embodiments, there can be a plurality of proximal neural electrode arrays, a plurality of distal nerve or muscle electrode arrays, a plurality of processors, and/or a plurality of detectors. These can all be interconnected or connected in groups and coordinate with each other based on various algorithms and/or desired results.

In use, a user may treat abnormal muscle activity in a patient by first identifying a dysfunctional or transferred nerve or nerve branch(es) or nerve segment(s) causing the dysfunction or the most dysfunction. For example, the orbicularis oculi muscle is innervated by several distal branches or segments of the facial nerve. Ocular synkinesis following aberrant neuronal recovery may be treated by highly selective neurectomy; this procedure involves resection of some of the distal facial nerve branches or segments supplying motor axonal input to the orbicularis oculi muscle to reduce the hyperactivity of the muscle. It is not currently possible to readily identify which one of the distal branches or segments may be most responsible for the dysfunction. The user may attach a plurality of electrode arrays to the dysfunctional or transferred distal nerve branches or segments supplying the dysfunctional or transferred muscle, and deliver electrical neural blockade signals in various combinations while the patient reproduces the action that induces the synkinesis. In this fashion, the nerve branches or segments most responsible for the dysfunction may be readily identified. The user may then opt to perform selective neurectomy of the identified branches or segments.

Examples

Neural blockade by means of HFAC can be used with dysfunctional or transferred nerves or nerve transfer procedures done anywhere in the body. Re-establishment of any form of motor neuron input is important in the prevention of denervation atrophy of muscle, however, triggering of the re-established neural input to restore exactly desired function is difficult to achieve. Illustrative examples can include the system's use in masseteric or hypoglossal transfer to distal facial nerve branch(es) or segment(s), its use in proximal blockade of the native facial nerve following Bell's palsy induced aberrant regeneration, its use in interposition graft repair of facial nerve defects (which result in aberrant regeneration). The system can also be used in the larynx following injury to the recurrent laryngeal nerve (RLN), a nerve which controls both the vocal fold adductors and abductors. Following neural injury, coordinated vocal fold movement is lost, leading to airway obstruction (too adducted) or aspiration and voice hoarseness/weakness (too abducted). Motor neuron input could thus be restored to the vocal fold musculature using a direct nerve repair of the RLN, interposition graft repair of the RLN, or nerve transfer to the RLN (for example, phrenic nerve branch or segment, ansa cervicalis nerve transfer, hypoglossal nerve transfer, and accessory nerve transfer). The system utilizing proximal HFAC neural blockade could then be applied (for instance using a bipolar neural cuff) to the dysfunctional or transferred nerve, with distal targeted and controlled stimulation of the adductors and abductors (such as by using small implantable electrodes and direct muscle stimulation), based off of a control signal/movement obtained from the contralateral (functioning) vocal fold, or other control signal to trigger glottis opening (for example pleural pressure transducer similar to that used with the implantable Inspire Sleep Apnea system).

Figure 14:
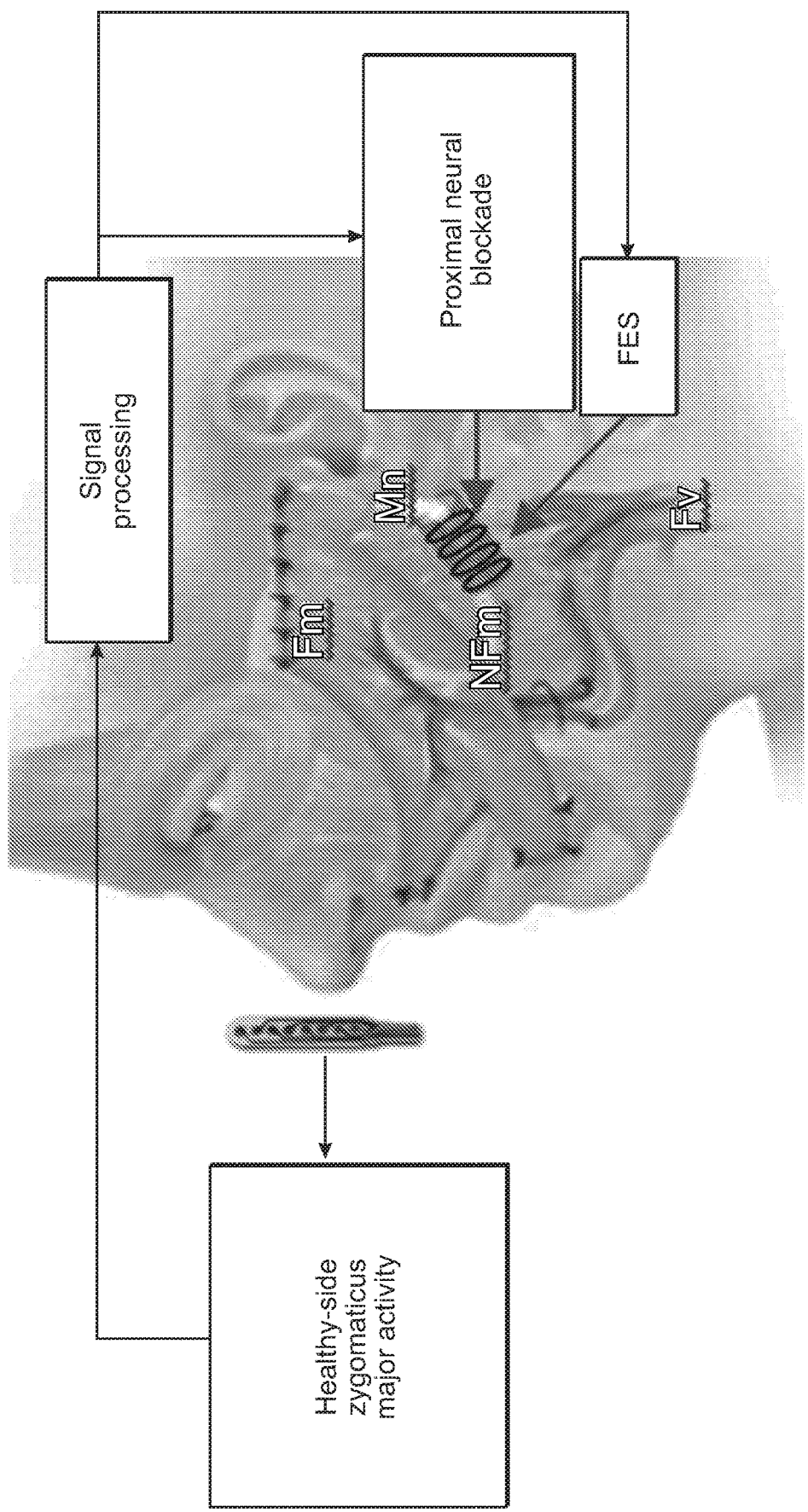
FIG. 14 illustrates the application of paradigm for electrical neural blockade in a human subject and functional stimulation of neuromusculature following nerve and muscle transfer, in this example for reanimation of spontaneous smile.

A non-limiting, illustrative example is free muscle transfer for reanimation of a smile. Currently, this procedure involves transfer of a branch or segment of healthy muscle from a distant site of the body (for example, gracilis muscle, latissimus dorsi, pectoralis minor) together with an artery, vein, and nerve that supply the particular muscle branch or segment. The free muscle is inset in the face of a patient with facial paralysis in a fashion that pulls the oral commissure laterally and superiorly to reproduce smile dynamics with activation (contraction) of the transferred muscle. Neural innervation to such free muscle is provided through nerve transfer, either using a cross-face nerve graft (i.e., signal arises from the contralateral facial nerve), or transfer of another motor nerve, such as branches or segments of the trigeminal nerve (for example, masseteric branch or segment), or others (for example, the hypoglassal nerve, the accessory nerve, etc.). Current limitations of cross-face nerve grafting include a high risk of failure (which would result in no triggering of the transferred muscle), nerve autograft requirement and associated donor site morbidity, and a risk of weakening the healthy side smile. For these reasons, other motor nerves are more commonly used in transfer procedures to innervate the transferred muscle. However, such transfers are also associated with severe limitations, which include undesired triggering of the transferred muscle (for instance an involuntary muscle activation with chewing in the case of motor trigeminal nerve transfer or with articulation and swallowing with a hypoglassal nerve transfer), as is further illustrated in FIG. 14. For example, FIG. 14 illustrates application of paradigm for reanimation of spontaneous smile in human patients undergoing nerve and free muscle transfer. An input signal is detected, in this case being the electromyography (EMG) activity of the contralateral zygomaticus major muscle using a single implanted epimysial electrode array. The signal serves as the input to a signal processor and generator whose output is a functional electrical stimulation (FES) signal applied distally to the transferred nerve or muscle to effect the desired contraction of the free muscle (Fm). A proximal neural blockade signal is delivered to eliminate undesired prandial activation of the transferred free muscle. In this example, a single 4-channel nerve cuff electrode array is implanted around the transferred nerve (in this example, the masseteric segment of the trigeminal nerve—Mn) and leads connected to the signal generator. (Fv—facial vessels, NFm—nerve to transferred free muscle).

The proximal neural blockade of the transferred nerve could be used during waking hours to inhibit undesired activation coupled with distal functional electrical stimulation that would be driven by contraction of the contralateral healthy side smile musculature (again in the case of reanimation of a smile). Such contraction of the contralateral healthy side musculature can be detected in open-loop fashion via emitted electrical activity of said musculature (such as EMG activity through the use of implanted electrodes), or through closed-loop fashion via detection of displacement (such as length) changes of the musculature (such as measured by impedance changes of the musculature or contact probe overlying said musculature). A signal processing algorithm can be used with inputs of healthy side activity signals and with outputs of functional electrical stimulation signals to the nerve supplying the transferred free muscle.

Another non-limiting example can include setting of highly selective neurectomy (HSN) for patients with ocular synkinesis following facial nerve insult and incomplete synkinetic recovery. HSN is based on the principle of redundancy of innervation to facial mimetic muscles. For instance, it is readily possible to identify about 3 to 6 or more terminal facial nerve branches or segments to the orbicularis oculi muscles. In patients with ocular synkinesis (for example aberrant eye closure with mimetic movement such as smiling), HSN may be of benefit in improving their symptoms. HSN involves a two-stage procedure; in the first stage, a facial skin flap is elevated under general anaesthetic, and multiple terminal facial nerve branches or segments to the synkinetic muscle are identified. Next, the patient is awoken and successive facial nerve branches or segments are cut until the desired effect is achieved (reduction of synkinesis with maintenance of voluntary eye closure). The system herein (and HFAC in particular) improves techniques and outcomes in HSN by providing a readily reversible means of observing what the effect of loss of neural input to combinations of the various terminal branches or segments would achieve prior to permanently dividing the nerve. For example, a neural cuff would be placed around each terminal branch or segment and connected to a multichannel signal generator, allowing for all possible permutations of neural blockade to be observed prior to permanent nerve sectioning. As onset of neural blockade with HFAC occurs within seconds and complete reversal within 500 ms, the system herein has strong clinical application.

In another non-limiting example, HFAC neural blockade is combined with distal nerve or target muscle stimulation from a multichannel signal generator capable of outputting either inhibitory HFAC or stimulatory electrical signals or both simultaneously to paired electrodes implanted into each distal nerve/mimetic muscle complex in the synkinetic face. Clinical use of HFAC is limited due to an onset response, whereby brief tetanic contraction of the target muscle occurs before the onset of muscle flaccidity and neural blockade. Furthermore, its use is also limited by a slight delay in the recovery of nerve excitability on the order of tens or hundreds of ms. Such a delay is inadequate to obtain symmetric facial movements to the eye of the human observer, which will detect an asymmetry if facial muscle excursion is not symmetric within about 40 ms. However, HFAC using a bipolar neural cuff produces a localized nerve block with preservation of distal nerve and muscle excitability. Thus, inhibitory signals of the present system could be set to "always on" during wakeful hours, blocking aberrant synkinetic signals arising from the proximal nerve, while the distal nerve and/or muscle itself could be selectively rapidly stimulated (within 40 ms) to mimic contractions of the contralateral face during voluntary and involuntary/spontaneous mimetic movements. Selective stimulation of individual synkinetic/flaccid muscles of the hemi-paralyzed face would be controlled through communication with a multichannel signal detector and processor to the corresponding distal branches or segments or target muscles of the contralateral healthy facial nerve/muscle complexes (as discussed in detail above).

The present system can also apply to unilateral motor nerve disorders where symmetric motion with the contralateral side is desired and synkinesis is problematic. Such is the case with injury to the recurrent laryngeal nerve, a motor nerve containing fibers both to vocal fold adductors and abductors. The present system can also apply to unilateral injury to the phrenic nerve, to restore symmetric diaphragm motion. Furthermore, the system herein can participate in reanimation of more complex peripheral motor nerve injuries, such as where the intended motion is often not simply a mirror image of a contralateral functioning side (such as in the case of brachial plexus injury), but where synkinesis is problematic. In such an embodiment, proximal electrical neural inhibition could be coupled with sophisticated processors to regulate distal stimulation of the nerve fibers or target muscles to achieve the desired complex motion. In place of input signals from the contralateral side (such as in facial paralysis, where symmetry with the contralateral side is desired) such processors could be programmed to receive other signals (such as voice input) to trigger a desired distal stimulation firing pattern.

The present system thus allows proximal electrical neural blockade to control synkinesis while selective distal stimulation provides precisely timed specific muscle contraction. When multiple electrodes are used in the present system, processing algorithms can be readily used and designed to achieve the desired motion. The reversibility of the electrical neural blockade allows for maintenance of physiologic neural innervation to the muscle and prevention of denervation atrophy.

Figure 3:
FIG. 3 illustrates placement of electrodes on the facial nerve in a live anesthetized rat.
Figure 4:
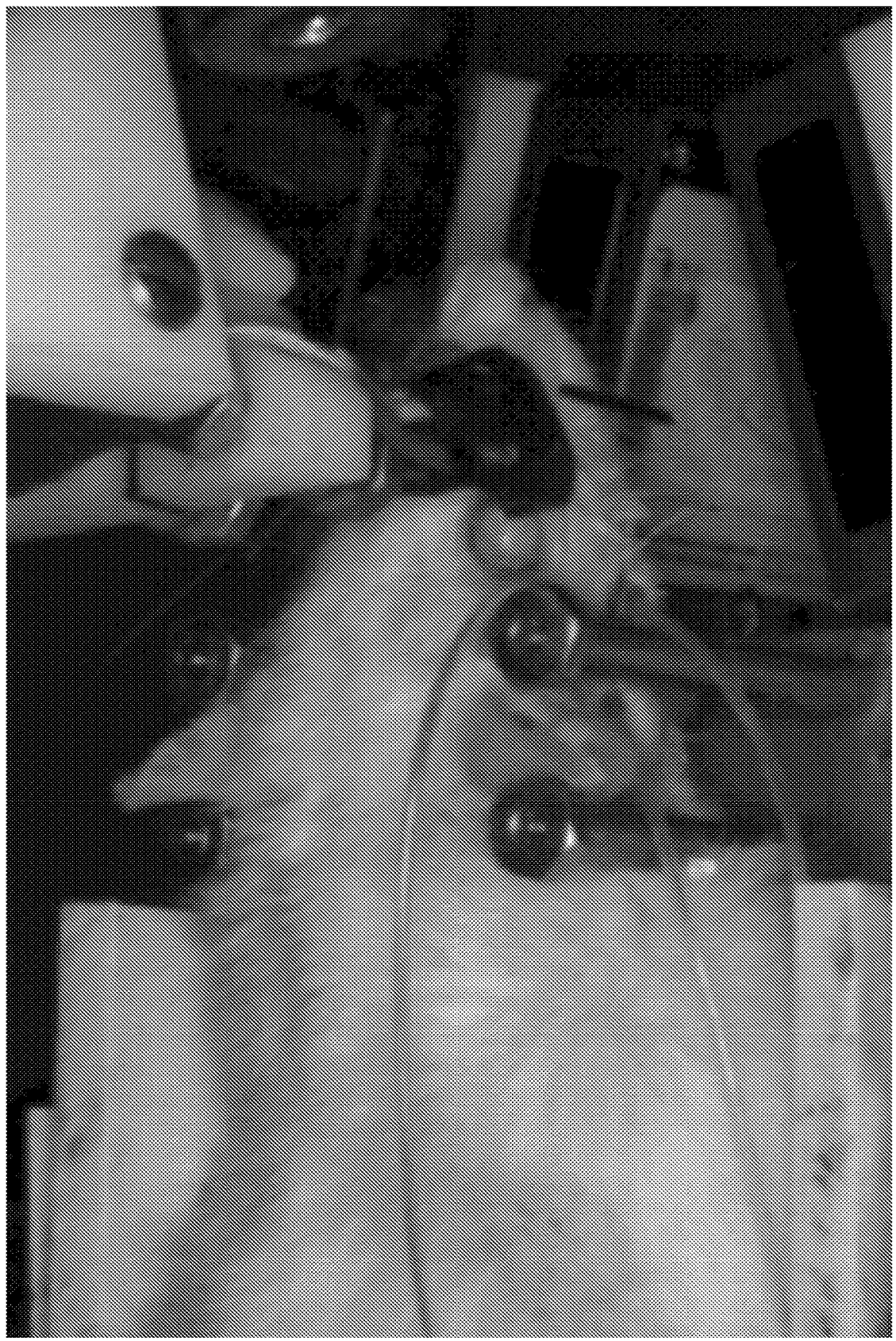
FIG. 4 illustrates positioning of the rat (an art-recognized model for peripheral motor nerve injury, synkinesis and related pathologies described herein) of FIG. 3 when quantifying whisker displacement in response to electrical stimuli.
Figure 5A:
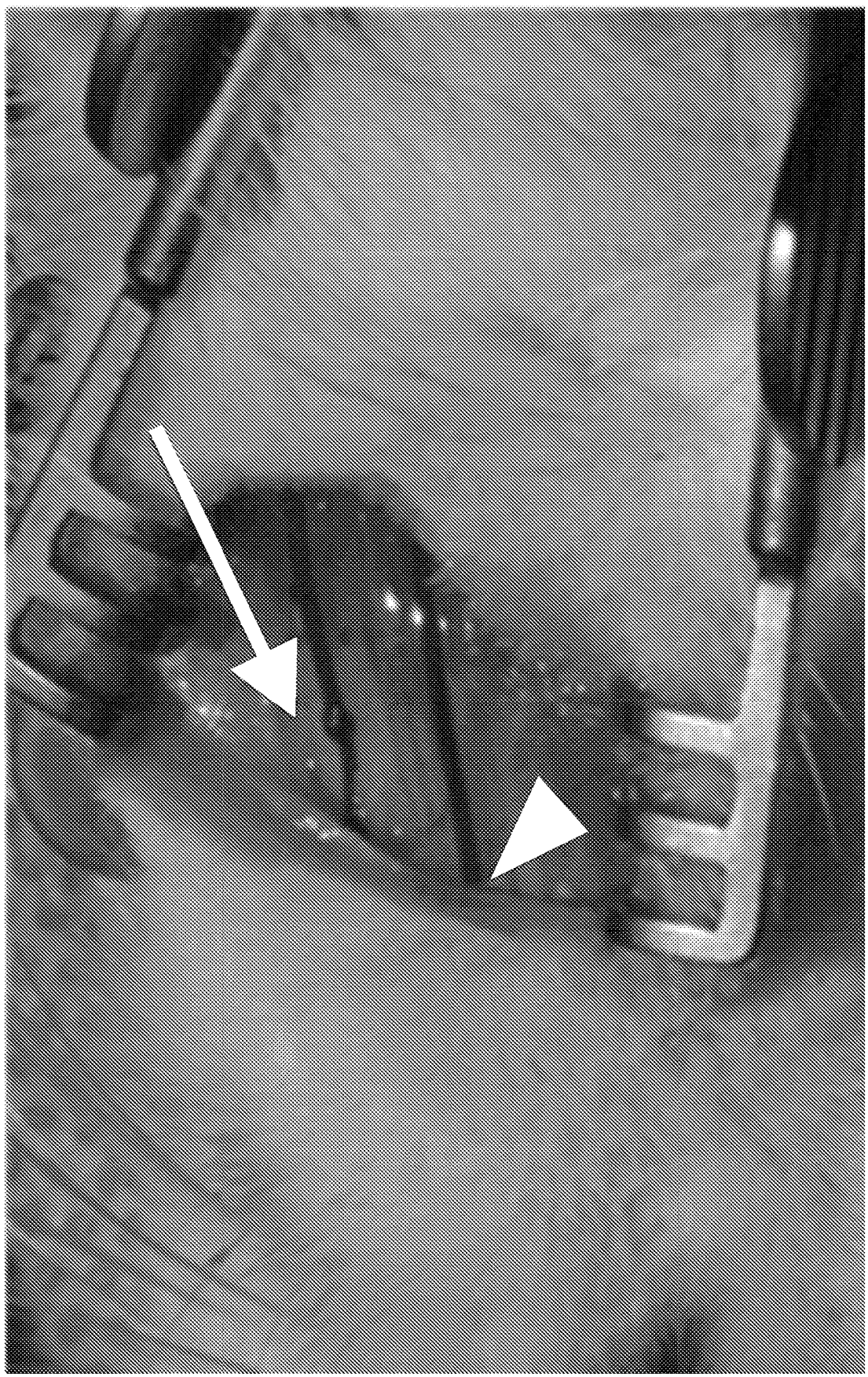
FIG. 5A illustrates sensing and signal delivery electrode arrays implanted into the rat face.
Figure 5B:
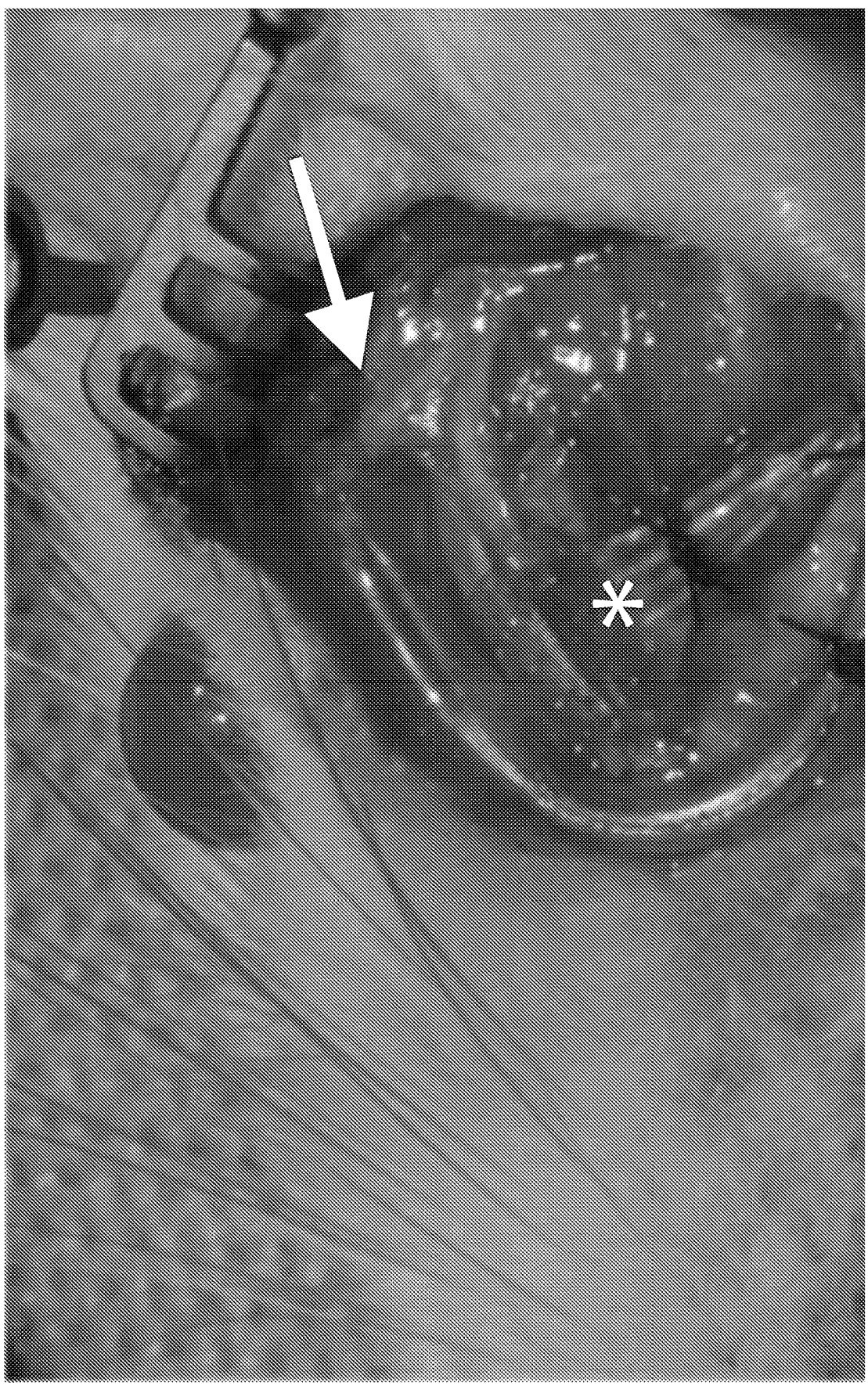
FIG. 5B illustrates sensing and signal delivery electrode arrays implanted into the rat face, as illustrated in FIG. 5A.
Figure 6:
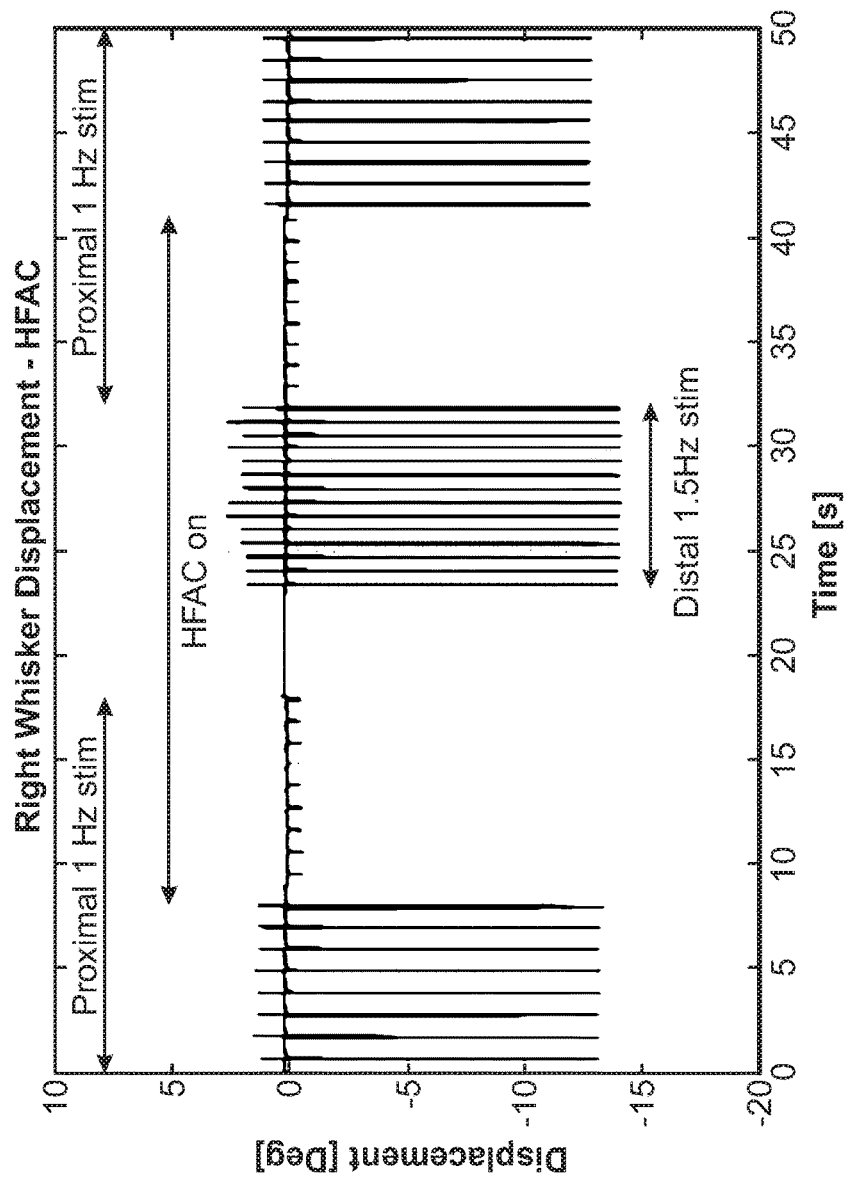
FIG. 6 illustrates the experimental setup with the rat of FIG. 3 with corresponding results.
Figure 6:
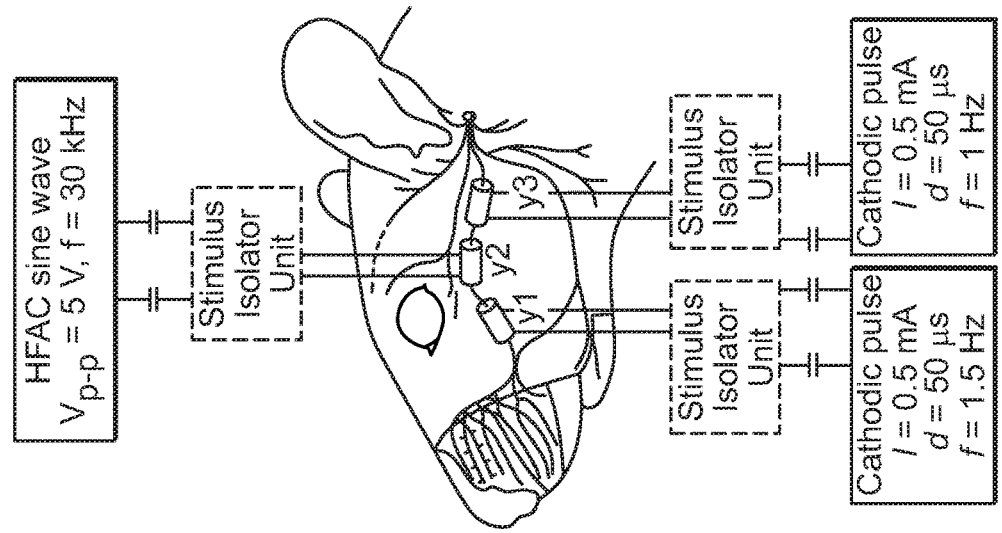

An embodiment of the present system has been applied to a live laboratory animal model, and specifically the application of localized neural blockade using bipolar neural cuff electrodes (NCEs) (Microprobes for Life Sciences, custom made silicone neural cuffs, platinum/Iridium electrodes, 1.0 mm inner diameter, 1 mm electrode spacing distance, 2 mm of silicone distal to each electrode) to a cranial nerve. FIG. 3 demonstrates placement of three such electrodes in a live anesthetized rat model on the buccal branch or segment of the facial nerve (FN), a motor nerve which controls whisker movement in the rat, illustrating 3 bipolar NCEs in position around the buccal branch of the rat FN. FIG. 4 demonstrates positioning of the rat in the field of laser micrometers to quantify whisker displacement, illustrating an anesthetized rat with implanted NCEs in head fixation for recording whisker displacement. FIGS. 5A and 5B demonstrate sensing and signal delivery electrode arrays implanted into the rat face. In this realization, a proximal cathodic stimulation pulse (i.e., to trigger whisker movement) is delivered at 1 Hz using the proximal bipolar NCE. The middle bipolar neural cuff is used to deliver a neural blockade signal (high-frequency alternative current, in constant voltage fashion using a 30 kHz sine wave with a peak-to-peak amplitude of 5V). The distal bipolar NCE is used to deliver another cathode stimulation pulse distal to the neural blockade at 1.5 Hz, and is used to demonstrate that the application of HFAC does not prevent distal excitability of the nerve-muscle complex. FIG. 5A illustrates an epimysial electrode array that is implanted underlying the orbicularis oculi (arrow) and whisker pad musculature (arrowhead), and FIG. 5B shows neural cuff electrode arrays that are implanted on zygomatic (arrow) and buccal (*) segments of the FN. The experimental setup with results, showing the effectiveness of HFAC in inducing a localized and reversible neural blockade through the use of a bipolar cuff electrode is summarized in FIG. 6. The experimental setup and results are shown from a trial of high frequency alternating current blockade of the FN in a live anaesthetized rat model. In the left of the image, bipolar neural cuff electrodes (y1, y2, y3) are implanted around the buccal branch of the facial nerve (1 mm spacing between platinum/iridium contacts). NCE-y1 and y3 are connected to cathodic stimulation pulses at 1.5 Hz and 1.0 Hz, respectively, through constant-current stimulus isolation units (SIUs). NCE-y2 is connected to a sine wave generator through a constant-voltage SIU. On the right of the figure, a displacement-time curve of a rat whisker is displayed under general anaesthesia under different paradigms: from t=0-7.5 s proximal stimulation through NCE-y3 is applied without HFAC at 1 Hz. When HFAC is turned on at t=7.5 s (through NCE-y2), the amplitude of displacement is reduced by approximately 90%. Displacement ceases when the proximal stimulation is switched off at t=17.5 s. At t=23 s, the distal stimulation at 1.5 Hz is applied through NCE-y1: identical maximum displacement is demonstrated despite persistent HFAC signal delivery at NCE-y2. At t=32 s, the distal stimulation is switched off, and the proximal stimulation at 1.0 Hz through NCE-y3 is switched back on. At t=42 s, the HFAC signal is switched off, and rapid return of whisker displacement is demonstrated. Neural or muscular stimulation parameters in humans are similar to those of other mammals. Stimulation parameters, such as waveform, amplitude, frequency, pulse duration and repetition rate may vary significantly depending on several factors. These factors include whether nerve or muscle is being stimulated and the desired dynamic force response of the muscle. For example, variable degrees of sustained contraction of human muscle may be achieved by delivery of a about 50 or about 60 Hz sinusoidal amplitude-modulated waveform with peak-to-peak voltage-controlled amplitudes of about 0.1 V—5 V to nerves. Such a stimulus may, for example, be used to trigger a smile of a particular excursion and duration. However, other muscle contraction may be elicited using much different stimulus parameters. For example, a blink response may be elicited using a single train of three biphasic square waves 40 µs in length having a peak-to-peak current-controlled amplitude in the range of 0.1 mA-2 mA. While stimulus signals may vary greatly, in general they should be charge-balanced to eliminate potential charge buildup, should not induce electrical or thermal neuropathy, and should be tailored for maximal energy efficiency (i.e., to use the smallest voltage or current amplitudes and durations) to achieve the desired functional muscular contraction. To achieve the same amount of contraction by means of direct muscle stimulation, 10-fold higher amplitudes are typically required.

Figure 10:
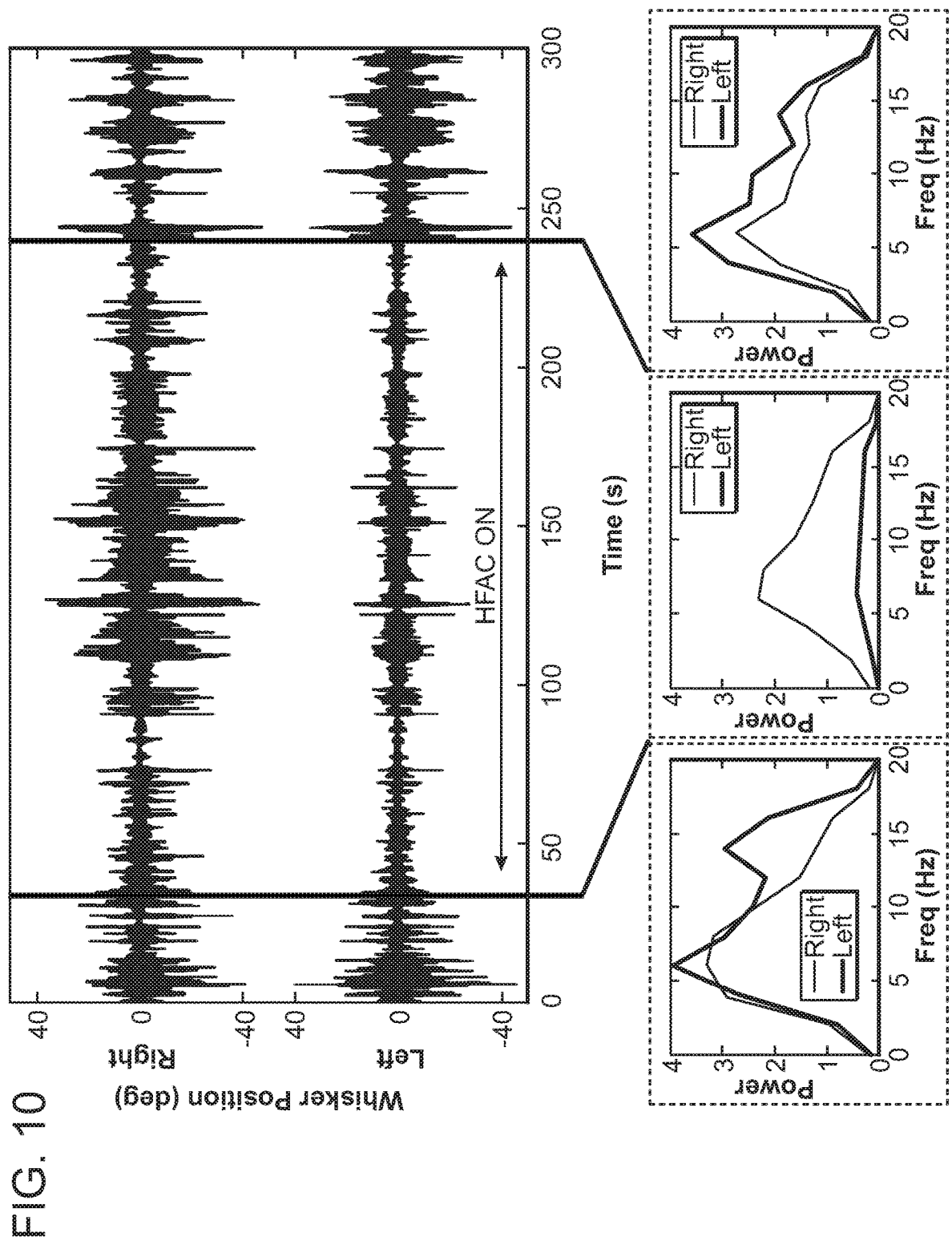
FIG. 10 illustrates the results of neural blockade of whisking in a live rat.

An embodiment of the neural blockade portion of the present system has been applied to a live awake laboratory animal model, and specifically the application of localized neural blockade by deliver of HFAC to the nerve controlling whisker function in a rat with FIG. 10 illustrates the results, showing neural blockade of whisking in a live rat. Constant neural blockade in the form of high frequency alternating current (HFAC) is delivered to the left buccal segment using a nerve cuff electrode array from t=30 s to t=240 s. The top row illustrates raw tracings of whisker displacement (including noise) over time. The bottom row shows power spectra (looking only at frequencies at which whisking occurs) demonstrating near equal left and right-sided whisking power during the periods immediately before and after HFAC delivery, with a dramatic drop on the left side seen with HFAC.

Figure 7:
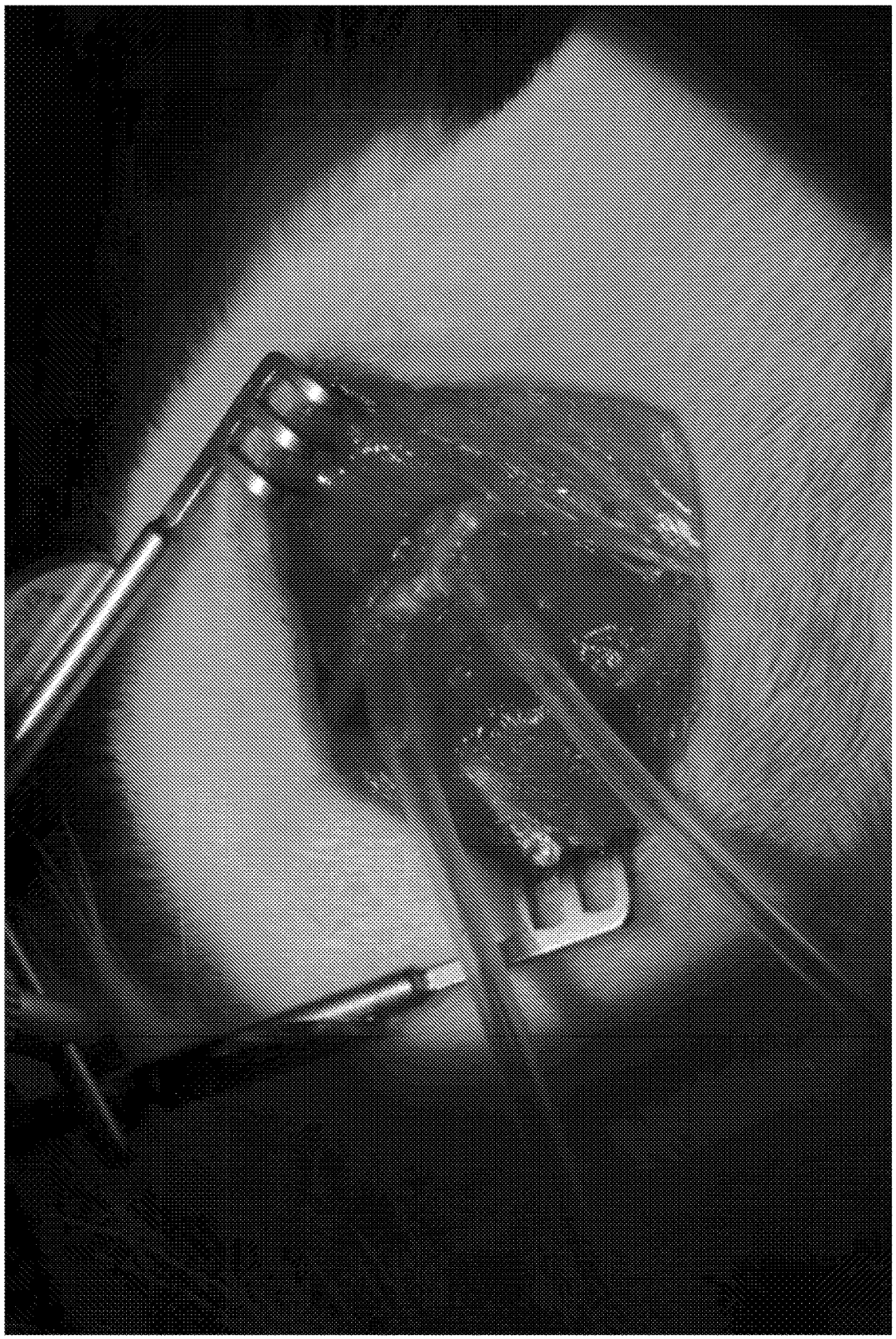
FIG. 7 illustrates placement of electrodes on the sciatic nerve in a live anesthetized rat.
Figure 8:
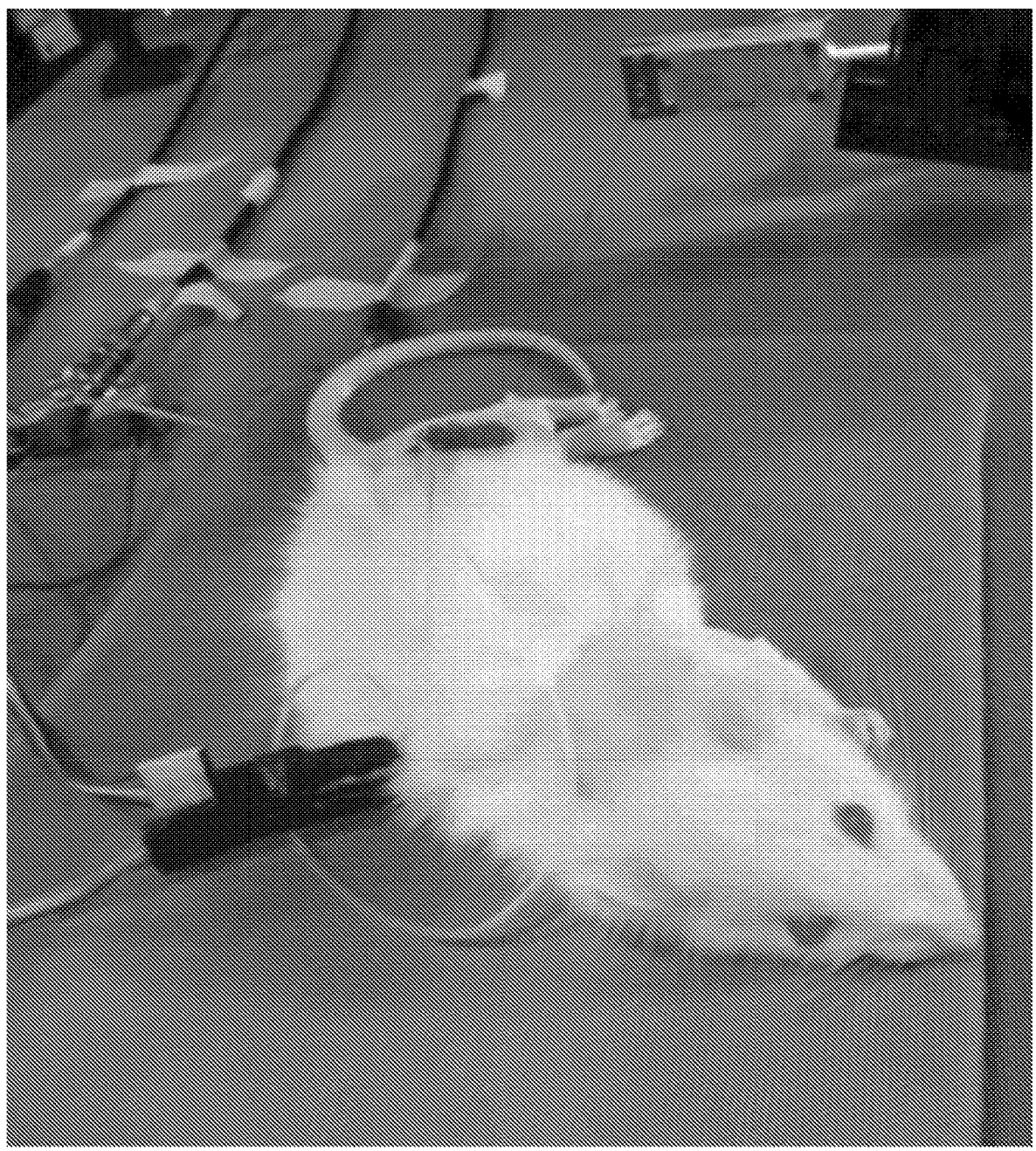
FIG. 8 illustrates position of the rat in FIG. 7 when quantifying hind limb force/tension in response to electrical stimuli.
Figure 9:
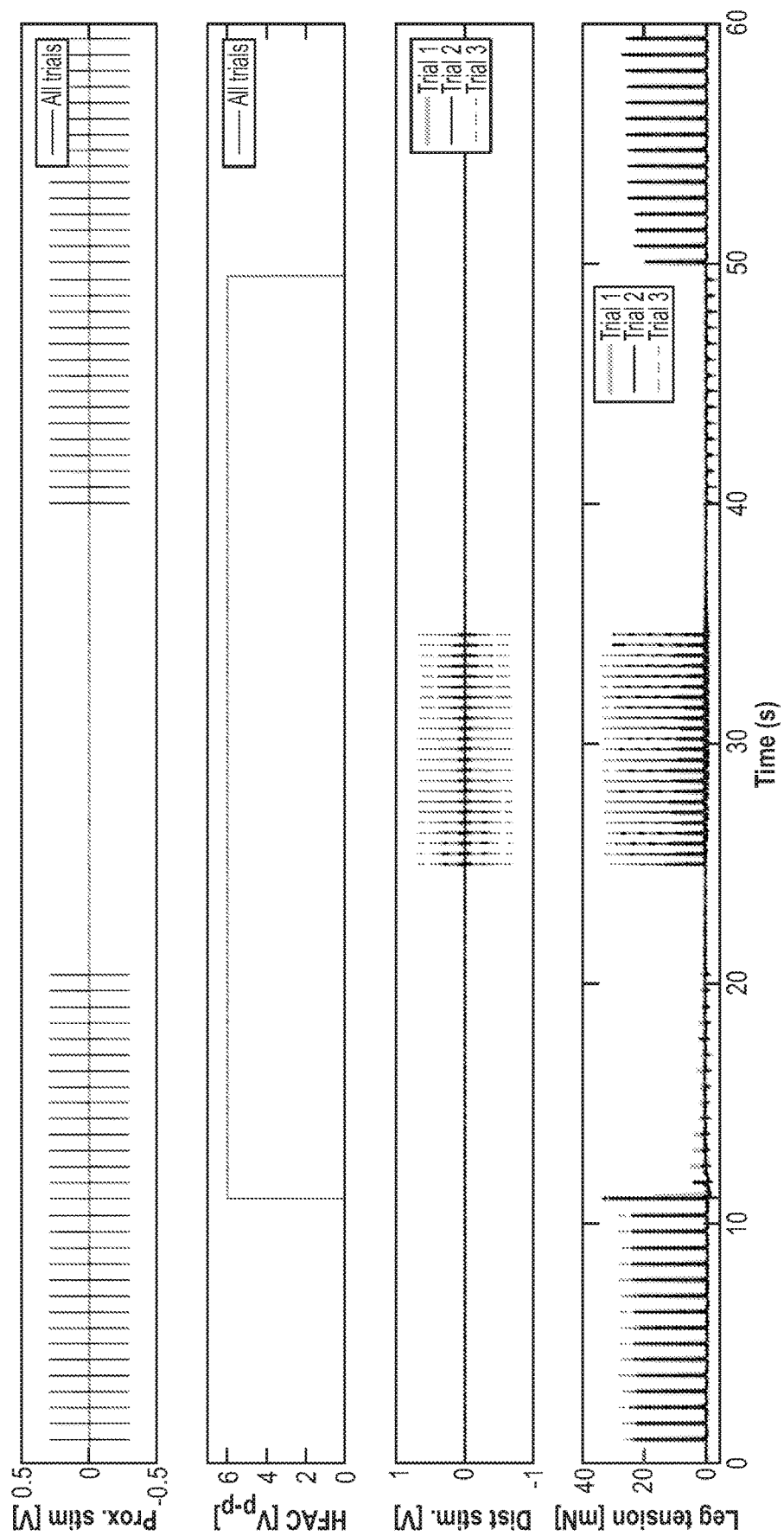
FIG. 9 illustrates the electrical stimulatory and blockade signals delivery to the sciatic nerve in real-time with corresponding force/tension response.

A further embodiment of the present system has been applied to a live laboratory animal model to a mixed sensory and motor peripheral nerve in the limb. FIG. 7 illustrates placement of electrodes on the sciatic nerve in a live anesthetized rat, showing nerve cuff electrodes in position around the sciatic nerve in a live anesthetized rat. The proximal cuff houses four platinum-iridium electrodes (two bipolar pairs), and the distal electrode houses two platinum-iridium electrodes (one bipolar pair) (Micro nerve cuff electrode, custom design, Microprobes for Life Sciences, Gaithersburg, Md.). The insulating material of the cuff is silicone. FIG. 8 illustrates position of the rat in FIG. 7 when quantifying hind limb force/tension in response to electrical stimuli, illustrating delivery of neural stimulation and blockade to the sciatic nerve in a live anesthetized rat. Leg contraction force is measured using a suture placed around the Achilles tendon attached to a force displacement transducer (Grass Instruments FT03, Natus Neurology Incorporated, Warwick, R.I.). Nerve cuff electrode leads are demonstrated exiting the leg, attached to pin connectors to an analog signal delivery device (Digidata 1320, Molecular Devices, Sunnyvale, Calif.). FIG. 9 illustrates the electrical stimulatory and blockade signals delivery to the sciatic nerve in real-time with corresponding force/tension response. FIG. 9 shows leg tension response to episodic stimulation with and without delivery of high-frequency alternating current (HFAC). The top row of FIG. 9 shows a voltage-controlled, charge-balanced (biphasic) square wave of 0.4 s pulse-width and 0.35 V amplitude being delivered at 1 Hz from t=9-20 s and from t=40-59 s proximal on the sciatic nerve using a bipolar nerve cuff electrode (BNCE). The second row illustrates a voltage-controlled HFAC (30 kHz, sinusoidal, peak-to-peak voltage [VP-P] of 6 V) being delivered from t=11-49.5 s on the sciatic nerve using a BNCE placed immediately distal to the proximal BNCE. The third row illustrates a voltage-controlled, charge-balanced (biphasic) square wave of 0.4 s pulse-width at amplitudes of 0.1 V, 0.4 V, and 0.7 V is delivered at 1.5 Hz from t=25-35 s using a BNCE placed distal to the BNCE delivering HFAC over 3 trials. The bottom row shows a force-tension response of the leg measured using a force displacement transducer (Grass Instruments FT03, Natus Neurology Incorporated, Warwick, R.I.); NB: Onset response of HFAC is demonstrated at t=11 s. Combined, this data demonstrates that a proximal neural stimulus may be effectively blocked using HFAC with maintenance of distal neuromusculature stimulability with proportional control. Software-controlled (pClamp 10, Molecular Devices, Sunnyvale, Calif.) stimulus signals were delivered in analog fashion using a digital-to-analog converter (Digidata 1320, Molecular Devices, Sunnyvale, Calif.). A software-controlled transistor-transistor logic (TTL) signal (pClamp 10, Molecular Devices, Sunnyvale, Calif.) was used to control HFAC delivery using a separate function generator (JYE Tech FG085).

Figure 11:
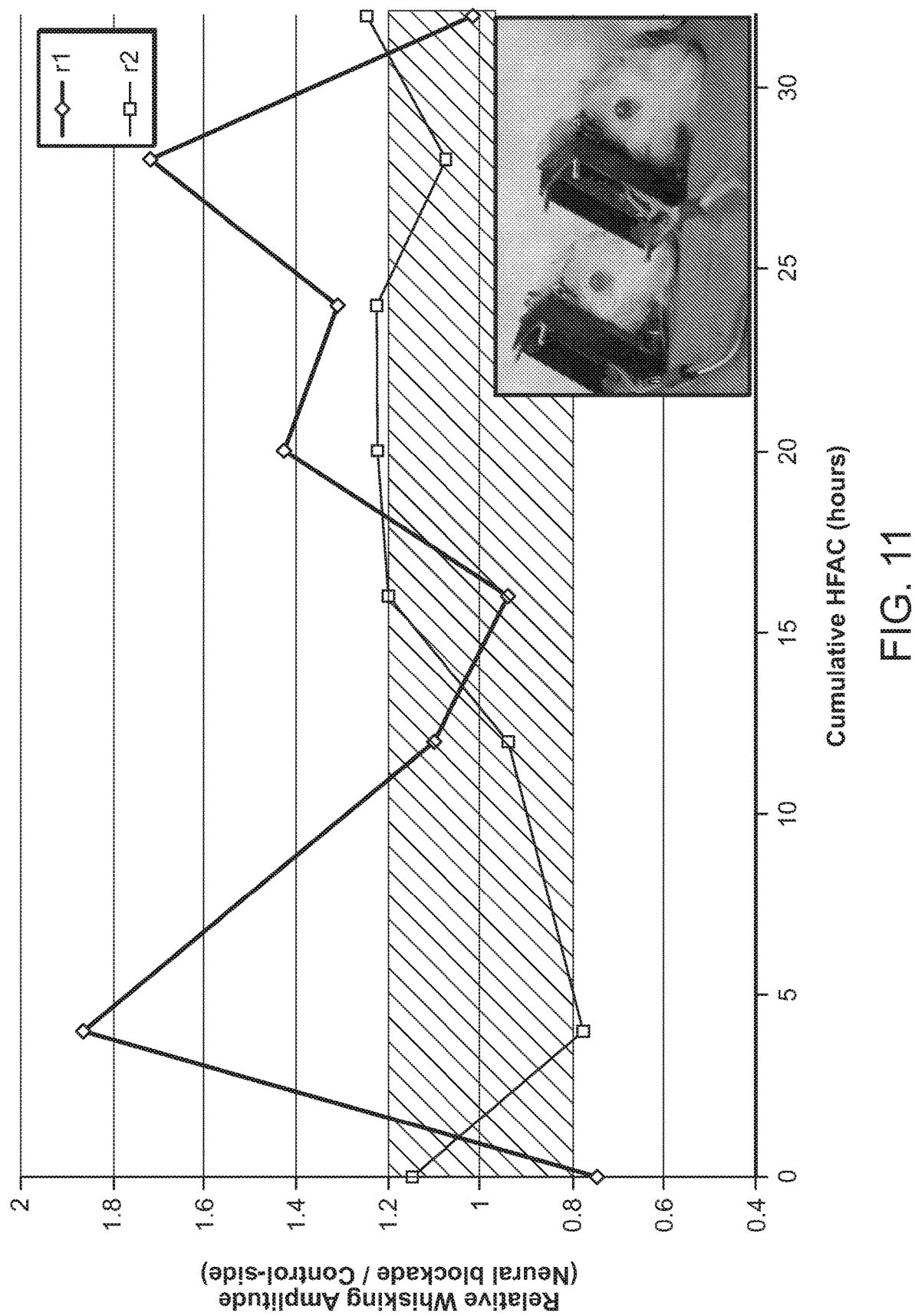
FIG. 11 illustrates functional whisking results following prolonged neural blockade by means of high frequency alternating current (HFAC) delivery in a rat model.
Figure 12:
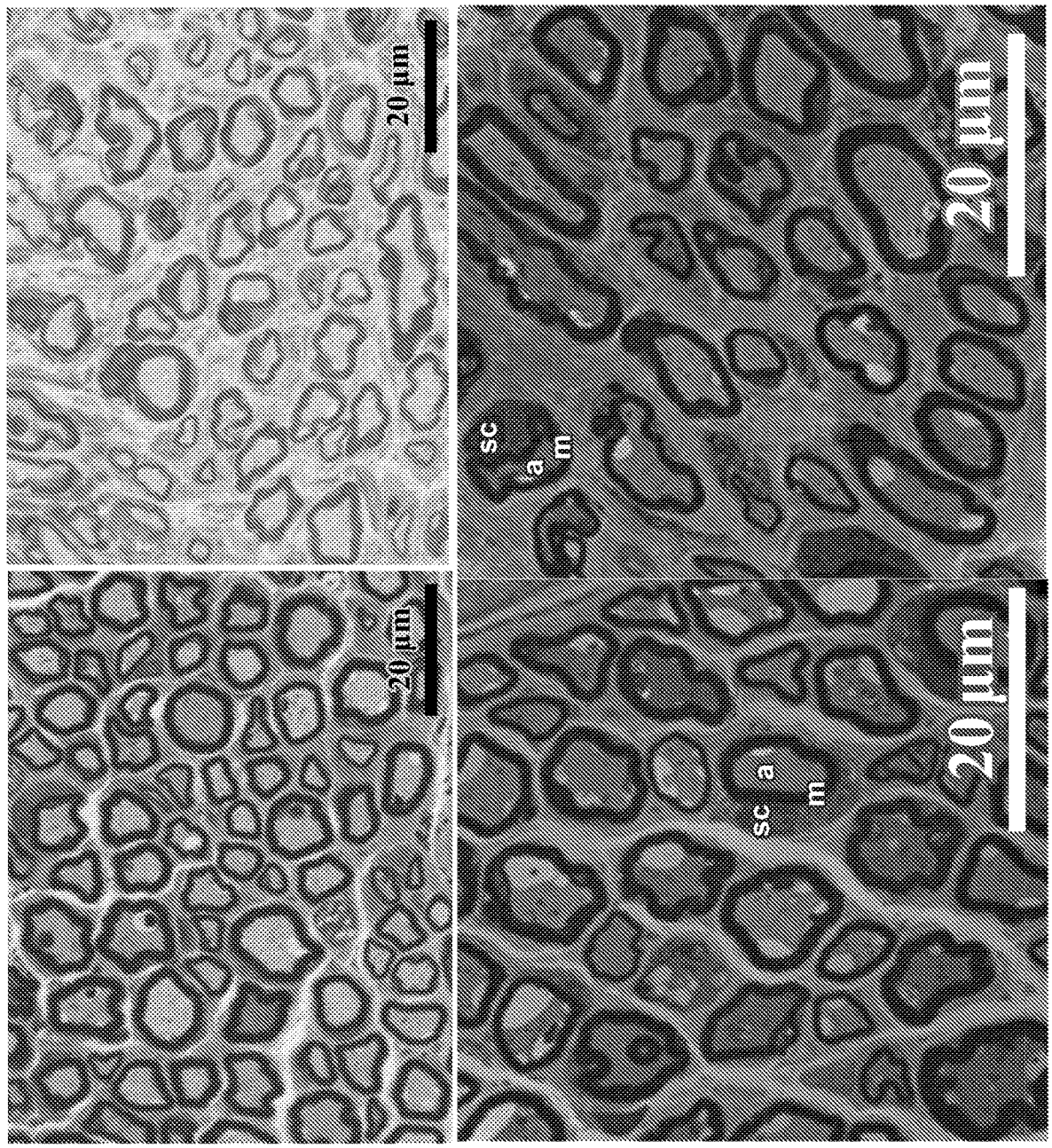
FIG. 12 illustrates light and transmission electron microscopy (TEM) of nerve following prolonged neural blockade delivery by means of high frequency alternative current (HFAC)
Figure 13:
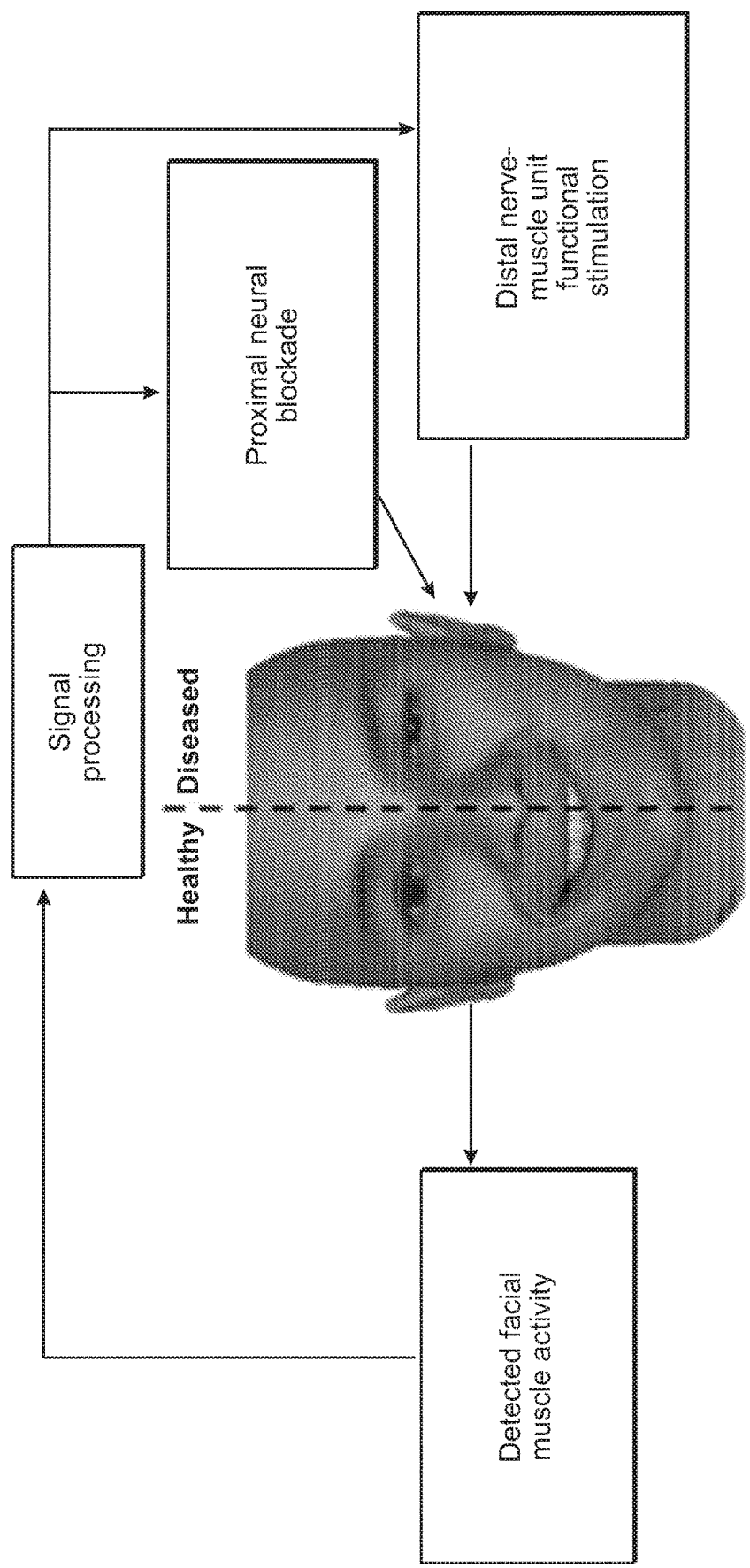
FIG. 13 illustrates a reanimation paradigm of electrical neural blockade and functional stimulation of distal neuromusculature in the face following aberrant recovery from facial nerve injury.

Further illustrations are shown in FIG. 11, providing functional whisking results following prolonged neural blockade by means of HFAC delivery in a rat model. For instance, relative maximal whisk amplitudes between left-face (implanted with nerve cuff electrode arrays on nerve controlling whisking with 4 hours of daily continuous HFAC delivery—see inset) and right-face (normal-side) demonstrate normal or stronger whisker displacements on the side to which HFAC was delivered (green bar approximates normal range). This indicates that prolonged delivery of electrical neural blockade in the form of HFAC does not damage the neuromusculature over time. FIG. 12 illustrates light and transmission electron microscopy (TEM) of nerve following prolonged neural blockade delivery by means of HFAC. For instance, normal axon appearance and myelination are seen for nerve within the cuff electrode (A) and distal to the cuff electrode (B) (1 ™ resin, toluidine blue, 400×). Normal ultrastructure is demonstrated on TEM for sectioned nerve within the cuff (C) and distal to the cuff (D), with labeled myelinated (m) axons (a) and supporting Schwann cells (sc) (2200×). This indicates that prolonged delivery of electrical neural blockade in the form of HFAC does not damage the nerve over time. FIG. 13 provides a reanimation paradigm in humans of electrical neural blockade and functional stimulation of distal neuromusculature in the human face following aberrant recovery from facial nerve injury. For example, healthy-side facial muscle activity is detected, for example through the use of epimysial electrode arrays to capture electromyography (EMG) signals. These healthy-side EMG signals then serve as inputs into a signal acquisition and generator platform where digital signal processing algorithms determine concordant output stimulatory signals through implanted electrode arrays on the diseased side distal nerve segments or target muscles to effect the desired contraction. Neural blockade is delivered proximally to the diseased-side nerve, for example using a constant high-frequency alternating current (HFAC) signal, to prevent undesirable muscle activation such as those causing synkinesis and facial muscle contracture. Combined, these components include a neuroprosthetic device.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

General Definitions and General Techniques

Unless specifically defined otherwise, all technical and scientific terms used herein shall be taken to have the same meaning as commonly understood by one of ordinary skill in the art (e.g., in cell culture, molecular genetics, and biochemistry).

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

As used herein, the terms "about" and "substantially" in the context of a numerical value or range means±10% of the numerical value or range recited or claimed, unless the context requires a more limited range.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

OTHER EMBODIMENTS

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed is:

1. A method of treating undesirable muscle activation in a subject comprising:
   identifying dysfunctional or transferred first neuromusculature;
   attaching an electrode array on the dysfunctional or transferred neuromusculature proximal to the target musculature;
   attaching a detector to healthy second neuromusculature, the first and second neuromusculature being part of a paired contralateral neuromusculature unit in the subject;
   detecting activity of the second neuromusculature;
   delivering a localized electrical neural blockade signal through the electrode array to inhibit propagation of neural depolarization at that point; and
   delivering a variable stimulus signal to the first neuromusculature in a functional manner distal to the point of neural blockade based on the detected activity of the second neuromusculature, the variable stimulus signal being variable by at least timing and degree of stimulation of the first neuromusculature.

2. The method of claim 1, wherein the electrical neural blockade signal comprises high frequency alternating current or a signal able to achieve localized and reversible neural blockade.

3. The method of claim 1, wherein the first neuromusculature comprises a facial nerve or facial nerve segment(s) or corresponding target musculature and the second neuromusculature comprises a paired contralateral facial nerve or facial nerve segment(s) or corresponding target musculature.

4. The method of claim 3, wherein delivering the localized electrical neural blockade signal and delivering the variable stimulus signal to the first neuromusculature cause the facial nerve or facial nerve segment(s) or corresponding target musculature of the first neuromusculature to mirror detected activity of the paired contralateral facial nerve or facial nerve segment(s) or corresponding target musculature of the second neuromusculature.

5. The method of claim 1, wherein the first neuromusculature comprises a vagal nerve or vagal nerve segment(s) or corresponding vagal nerve target musculature and the second neuromusculature comprises a paired contralateral vagal nerve or phrenic nerve or a segment or segments of the vagal nerve or phrenic nerve or corresponding vagal or phrenic nerve target musculature.

6. The method of claim 1, wherein detecting activity signals of the second neuromusculature includes detecting emitted electrical activity of the second neuromusculature.

7. The method of claim 1, wherein detecting activity of the other neuromusculature includes detecting signals corresponding to displacement, impedance, force, or pressure changes that arise due to the activity of the second neuromusculature.

8. The method of claim 1, wherein delivering the localized electrical neural blockade signal and delivering the variable stimulus signal to the dysfunctional or transferred neuromusculature are selectably performed during waking hours of the subject, during sleeping hours of the subject, or both.

9. The method of claim 1, wherein delivering the localized electrical neural blockade signal and delivering the variable stimulus signal to the first neuromusculature cause the first neuromusculature to mirror detected activity of the second neuromusculature.

10. The method of claim 1, wherein delivering the localized electrical neural blockade signal and delivering the variable stimulus signal to the first neuromusculature are selectably performed in real-time by the subject or a secondary user.

11. A system of neuromusculature treatment comprising:
an electrode array configured to attach proximally along dysfunctional or transferred first neuromusculature and deliver an electrical neural blockade signal;
a detector configured to detect activity of healthy second neuromusculature, the first and second neuromusculature being part of a paired contralateral neuromusculature unit;
a stimulating nerve or muscle electrode array configured to attach distally along the first neuromusculature and apply a variable stimulatory signal to the first neuromusculature; and
a processor in communication with a signal generator, a power supply, the detector, the proximal electrode array, and the distal stimulating nerve or muscle electrode array, the processor being configured to provide stimulation instructions to the distal stimulating nerve or muscle electrode array and neural blockade instructions to the proximal electrode array based on activity signals detected by the detector of the second neuromusculature.

12. The system of claim 11, wherein the first neuromusculature comprises a facial nerve or facial nerve segment and its target musculature and the second neuromusculature comprises a contralateral facial nerve or facial nerve segment and its target musculature.

13. The system of claim 11, wherein the first neuromusculature comprises a vagal nerve or vagal nerve segment(s) or corresponding vagal nerve target musculature and the second neuromusculature comprises a paired contralateral vagal nerve or phrenic nerve or a segment or segments of the vagal nerve or phrenic nerve or corresponding vagal or phrenic nerve target musculature.

14. The system of claim 11, wherein the detector is configured to detect emitted electrical activity of the second neuromusculature.

15. The system of claim 11, wherein the detector is configured to detect signals corresponding to displacement, impedance, force, or pressure changes that arise due to the activity of the second neuromusculature.

16. The system of claim 11, wherein the system is selectably enabled during waking hours of a subject, during sleeping hours of a subject, or both.

17. The system of claim 11, wherein the stimulation instructions are configured to cause the first neuromusculature to mirror the activity signals detected by the detector of the second neuromusculature.

18. A device for neuromusculature treatment comprising:
a blockade electrode array configured to deliver an electrical neural blockade signal;
a stimulating electrode array configured to apply a variable stimulatory signal to first neuromusculature of a paired contralateral neuromuscular unit;
a detector configured to detect neural activity of second neuromusculature of the paired contralateral neuromuscular unit;
a signal generator;
a power supply; and
a processor in communication with the signal generator, the power supply, the detector, the blockade electrode array, and the stimulating electrode array, the processor being configured to provide stimulation instructions to the stimulating electrode array and neural blockade instructions to the blockade electrode array based on signals detected by the detector of the second neuromusculature.

19. The device of claim 18, wherein the detector is configured to detect signals corresponding to displacement, impedance, force, or pressure changes.

20. The device of claim 18, wherein the stimulation instructions are configured to cause the first neuromusculature to mirror the signals detected by the detector of the second neuromusculature.

* * * * *